(12) United States Patent
Kiyama et al.

(10) Patent No.: US 10,087,409 B2
(45) Date of Patent: Oct. 2, 2018

(54) CELL-CULTURING VESSEL AND CELL-CULTURING DEVICE USING SAME

(71) Applicant: Hitachi, Ltd., Tokyo (JP)

(72) Inventors: Masaharu Kiyama, Tokyo (JP); Guangbin Zhou, Tokyo (JP); Ryota Nakajima, Tokyo (JP); Takayuki Nozaki, Tokyo (JP); Naoko Senda, Tokyo (JP); Shizu Matsuoka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 537 days.

(21) Appl. No.: 14/426,457

(22) PCT Filed: Sep. 26, 2012

(86) PCT No.: PCT/JP2012/074667
§ 371 (c)(1),
(2) Date: Mar. 6, 2015

(87) PCT Pub. No.: WO2014/049701
PCT Pub. Date: Apr. 3, 2014

(65) Prior Publication Data
US 2015/0218503 A1    Aug. 6, 2015

(51) Int. Cl.
*C12M 1/22* (2006.01)
*C12M 1/00* (2006.01)
*C12M 1/42* (2006.01)
*C12M 3/00* (2006.01)
*C12M 1/12* (2006.01)
*C12M 1/36* (2006.01)

(52) U.S. Cl.
CPC ............ *C12M 23/42* (2013.01); *C12M 23/10* (2013.01); *C12M 23/22* (2013.01); *C12M 23/34* (2013.01); *C12M 23/38* (2013.01);

*C12M 23/40* (2013.01); *C12M 25/04* (2013.01); *C12M 29/00* (2013.01); *C12M 35/08* (2013.01); *C12M 37/00* (2013.01); *C12M 41/48* (2013.01)

(58) Field of Classification Search
CPC ...... C12M 23/34; C12M 23/58; C12M 23/12; C12M 23/40; C12M 23/44; C12M 29/04; C12M 35/08; C12M 37/02; C12M 37/04
USPC .......... 435/294.1, 297.1, 305.2, 305.3, 305.4
See application file for complete search history.

(56) References Cited

U.S. PATENT DOCUMENTS

2015/0231628 A1* 8/2015 Nozaki .................. B01L 3/508
422/547

FOREIGN PATENT DOCUMENTS

| JP | 2005-151866 A | 6/2005 |
| JP | 2006-320304 A | 11/2006 |
| JP | 2007-312668 A | 12/2007 |

(Continued)

*Primary Examiner* — Nathan A Bowers
*Assistant Examiner* — Lydia Edwards
(74) *Attorney, Agent, or Firm* — Mattingly & Malur, PC

(57) ABSTRACT

Provided is a cell culturing vessel for holding and culturing cells. It has a first vessel that stores a culture medium and cells or only a culture medium, a second vessel that is placed above the first vessel and stores a culture medium and cells or only a culture medium, a main vessel that holds the first vessel and houses the second vessel, and a lid member that engages with the main vessel. The main vessel has a pressing member that fixes and holds the first vessel in the main vessel and the second vessel is eccentrically held in the first vessel by the pressing member.

7 Claims, 14 Drawing Sheets

(56) References Cited

FOREIGN PATENT DOCUMENTS

| | | | |
|---|---|---|---|
| JP | 2008-271912 A | 11/2008 | |
| JP | 4602460 B1 | 10/2010 | |
| JP | WO 2014041593 A1 * | 3/2014 | ........... A01N 1/0242 |
| WO | 2012/008368 A1 | 1/2012 | |

* cited by examiner

CELL-CULTURING VESSEL AND CELL-CULTURING DEVICE USING SAME

BACKGROUND OF THE INVENTION

1. Field of the Invention

The present invention relates to a cell culturing vessel for culturing cells and a cell culturing device using the vessel.

2. Description of the Related Art

In regenerative medicine performed to treat diseases by using cells of patients themselves or others, cells collected from living bodies are used for transplantation therapy after cultured to increase their number or formed into a desired tissue form. Cells to be used for therapy should be cultured in a cell culturing clean room called "Cell Processing Center (CPC)" in accordance with GMP (Good Manufacturing Practice). The problems here are that preparation of cells for one patient requires much effort and cost because cell culture is performed manually by technical experts and that manual operation carries a biological contamination risk.

As a means for solving the above-mentioned problems, a device for automating a cell culturing step in a closed system has been developed. By using a closed system culturing vessel not requiring an opening or closing operation of its lid, automation of a cell culturing step and reduction in biological pollution risk can be achieved simultaneously.

On the other hand, there are two cell types, that is, a cell type that needs a growth factor produced by trophocytes called "feeder cells" during proliferation and a cell type that does not need this growth factor. The cell type such as ES (embryonic stem) cells, iPS (induced pluripotent stem) cells, cutaneous epithelial cells, corneal epithelial cells, and oral mucosal epithelial cells often need feeder cells. When cultured cells are used for therapy, feeder cells and cells to be used in therapy are desirably separated during culturing and are therefore cultured desirably in a cell culturing vessel having two culturing layers.

As a means for solving the above-mentioned problem, a cell culturing vessel and a culturing device as shown in Japanese Patent No. 4602460 have been proposed. According to this document, the cell culturing vessel has two culturing layers and the culturing device is equipped with a flow channel for supplying or discharging cells or a medium and a cell observation unit so that epithelial cells such as cutaneous epithelial cells, corneal epithelial cells, and oral mucosal epithelial cells can be automatically cultured in a closed system and the cultured state can be observed.

As a device capable of achieving automatic culturing of cell types not requiring feeder cells during their growth, a culturing device as shown in Patent Document 2 is proposed. The automatic culturing device disclosed in this document cultures cells, mainly stem cells, in a single culturing layer.

Japanese Patent Laid-Open No. 2005-151866 discloses a method of observing the adhesion state between cells and a substrate material.

SUMMARY OF THE INVENTION

It usually takes two or three weeks to complete culturing of cells and the growth of the cells during this period is observed making use of a microscope or a phase contrast microscope. A culturing vessel made of a polystyrene or polycarbonate material having light permeability is therefore used. As culturing proceeds, the above-mentioned cell type adheres to the bottom of the culturing vessel and spreads and then becomes a cell sheet with thickness. For stable adhesion of cells to the culturing vessel, modification treatment for converting the essentially hydrophobic surface of polystyrene or the like is necessary. A commercially available culture dish has already been subjected to hydrophilic treatment by corona discharge processing. Using a cell culturing vessel having two culturing layers as shown in Japanese Patent No. 4602460 has however the following four problems.

The first problem is that when a closed system culturing vessel is used, a joint member, a tubular member, and the like are provided for delivering or discharging a culture medium to or from the vessel. They are placed diagonally to a circular culture surface of the vessel and block a light irradiated from a light source in microscopic observation, making it difficult to obtain a clear observation image.

The automatic culturing device described in Japanese Patent Laid-Open No. 2007-312668 is, similar to the device of Japanese Patent No. 4602460, is an automatic culturing device mainly for culturing stem cells by using a closed system culturing container (culturing vessel). This culturing container is also equipped with a cell observation unit. It has an incubator for holding the container between the cell observation unit and the container. This document includes no specific description on the improvement in the constitution of the observation unit and an object to be observed.

Japanese Patent Laid-Open No. 2005-151866 describes a sample substrate holder. Although it does not include any specific description on a supply port and the like capable of delivery or discharge without disturbing an observation visual field, an example described herein is an open system vessel and does not overcome the above-mentioned problem that occurs in a closed system vessel due to necessity of liquid supply.

The second problem is that when a culture medium or the like is discharged from a culturing vessel, medium replacement is performed so that an old culture medium is pushed out with a new culture medium. This causes mixing of the new culture medium with the old one. Components of the old medium remaining in the culturing vessel may damage the reproducibility in cell culture. This means that during medium replacement, remaining of an old medium in the vessel should be reduced as much as possible.

The third problem is that with regard to a culture surface, the inner surface of the vessel has been subjected to the above-mentioned hydrophilic treatment, but a special shape of the culturing vessel itself prevents smooth hydrophilic treatment. In addition, a cost of the surface treatment increases a cost of the vessel. Further, the cell culture itself may have a risk of becoming unstable, depending on the state of the culture surface treatment.

The fourth problem is that in the related art, supply of a liquid to a culturing vessel is performed via a detachable tubular member, but when the tubular member is detached, the tubular member is exposed outside a cell culturing space. This may permit invasion of microorganism-containing particles from the outside.

In view the above-mentioned problems, the invention has been made. One of the objects of the invention is to provide a cell culturing vessel that enables clear cell observation in cell culturing.

One typical example of the present invention is as follows.

Provided is a cell culturing vessel for holding and culturing cells therein. It is equipped with a first vessel that stores a culture medium and a cell or only a culture medium, a second vessel that is placed above the first vessel and stores a culture medium and a cell or only a culture medium, a main vessel that holds the first vessel and houses the second vessel, and a lid member that engages with the main vessel. The main vessel has a pressing member that fixes and holds the first vessel in the main vessel and the second vessel is eccentrically held in the first vessel by the pressing member.

According to the cell culturing vessel of the invention, the second vessel is eccentrically held in the first vessel so that there is no obstacle that disturbs an observation visual field of a microscope or the like. This enables clear observation of the growth state of cultured cells.

DETAILED DESCRIPTION OF THE PREFERRED EMBODIMENTS

Figure 1A:
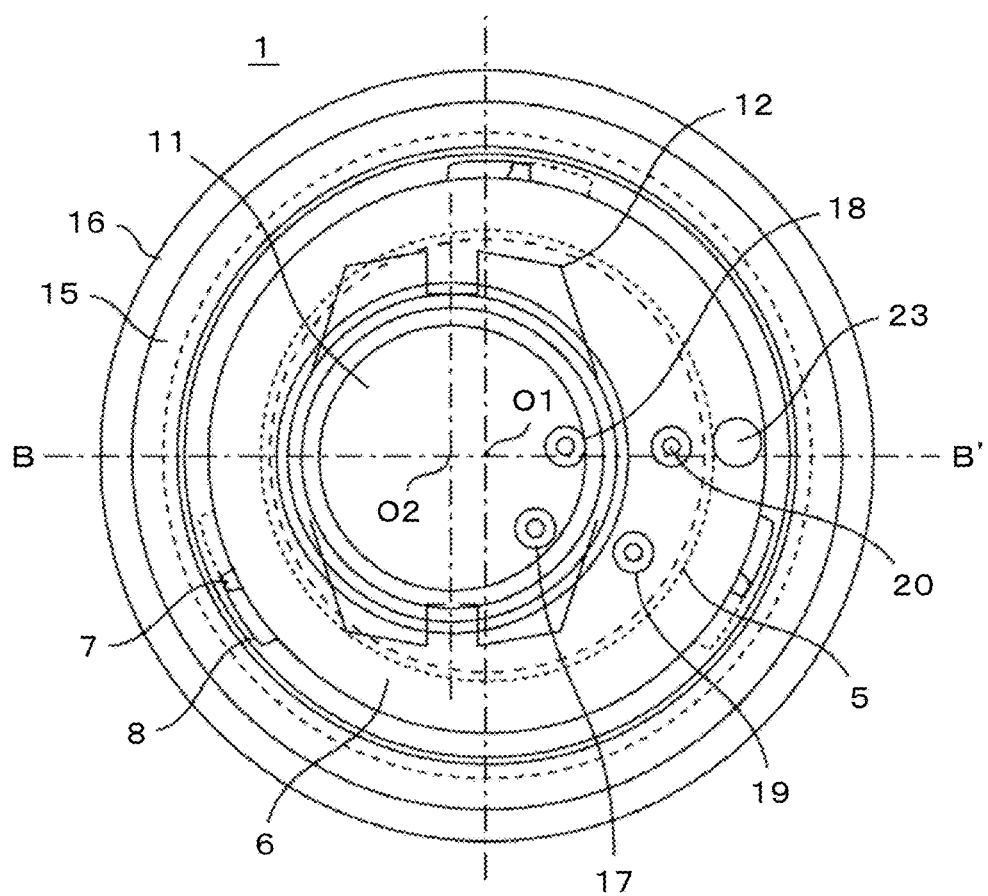
FIG. 1A is a plan view showing the structure of a cell culturing vessel according to First Example of the invention.

The cell culturing vessel and the cell culturing device using it according to the invention include a plurality of means for solving the above-mentioned problems. The following is one example of them.

Provided is a cell culturing vessel for holding and culturing cells. It is equipped with a first vessel that houses a culture medium and a cell or only the culture medium, a second vessel that is placed above the first vessel and houses a culture medium and a cell or only the culture medium, a main vessel that holds the first vessel and houses the second vessel, and a lid member that engages with the main vessel. The main vessel has a pressing member for fixing and holding the first vessel in the main vessel and the second vessel is eccentrically held in the first vessel by the pressing member.

In the above-mentioned cell culturing vessel, the lid member of the culturing vessel is equipped with a plurality of ducts that can be connected to outside flow channels and the ducts are placed in a region on one side of a center line of the second vessel.

Further, in the cell culturing vessel, the first vessel is fixed under pressure by the pressing member and the second vessel is fixed under pressure by the lid member.

Further, in the cell culturing vessel, the first vessel is fixed to the main vessel via an elastic body and has an outer surface exposed from the main vessel, the lid member is fixed via a second elastic body, and the culturing vessel is kept airtight.

Further, in the cell culturing vessel, a through-hole of the pressing member is smaller than the inner diameter of the first vessel and greater than the outer diameter of the second vessel.

Further, in the culturing vessel, an opening end of the duct that discharges a culture medium from the first vessel is placed close to the lowest point of the outer surface of the second vessel.

In a cell culturing device using the cell culturing vessel, the lid member of the culturing vessel is equipped with first, second, third, and fourth ducts that can be connected to an outside flow channel, these first to fourth ducts are placed in a region on one side of a center line of the second vessel, and in the region on one side, the first to fourth ducts are connected to a liquid delivery control means that controls supply or discharge of a culture medium to the first vessel or supply or discharge of a culture medium to the second vessel.

In the cell culturing device using the cell culturing vessel, the first vessel is fixed to the main vessel via an elastic body, has an outer surface exposed from the main vessel, and has a cell observation unit placed close and opposite to the culturing vessel.

With regard to the first problem, in the cell culturing vessel of the invention, a culture dish to be observed and a cell observation unit are constituted so that the culture dish having transparency is exposed from the outer surface of the closed culturing vessel and is placed opposite to the culturing vessel and a microscope or the like that obstructs an observation visual field is omitted. The first to fourth ports are placed collectively on one side of the center of first vessel in order to maximize the observation visual field. This enables clear observation of the growth state of cultured cells.

With regard to the second problem, in medium replacement operation, an old culture medium is discharged, followed by addition of a new culture medium so that remaining of the old culture medium is prevented. A discharge port is placed at the lowest point of the culture dish. When the culturing vessel is held at an arbitrary angle, a culture medium to be replaced gathers at the lowest point of each vessel, facilitating discharge by suction. In addition, the center of the first vessel is eccentric to that of the second vessel and a surface tension of a culture medium generated on the inside wall is small so that an amount of the culture medium remaining at the time of medium discharge operation decreases. By providing an opening end for medium discharge in the vicinity of the outside bottom portion of the second vessel, a collection amount of the old culture medium remaining between the inside bottom of the first vessel and the outside bottom surface of the second vessel can be increased when the culturing vessel is tilted.

With regard to the third problem, the surface condition can be kept stable because a surface-treated culture dish to be used manually can be used as the first vessel for culturing cells. This leads to stable cell culture. This culture dish is commercially available and a surface treatment cost can be reduced by using such a culture dish.

With regard to the fourth problem, that is, the contamination from the outside, invasion of microorganism-containing particles from the outside can be prevented because the culturing vessels and the flow channels use a completely closed system and do not have any structure exposed outside the culturing vessel. In the internal structure of the cell culturing vessel, the pressing member has a hollow node portion that acts as a side wall of the first vessel and splash of a feeder cell fluid generated during seeding of it in the first vessel can be prevented from reaching the inside of the second vessel with this node portion as a barrier.

The cell culturing device of the invention enables stable cell culture. Further, since it is provided with a unit that facilitates observation of a cultured state and is also provided with a unit capable of automatically culturing cells in a completely closed system, cells can be cultured stably under an antiseptic condition.

Various examples of the invention will hereinafter be described referring to accompanying drawings. These examples are merely examples for actualizing the invention and they do not limit the technical scope of the invention. In each drawing, similar components are identified by the same reference number. The term "culture liquid" as used herein is sometimes called "medium".

Example 1

First Example of the cell culturing vessel and the cell culturing device using the vessel, each according to the invention, will next be described, referring to FIGS. 1A to 7.
<Structure of Cell Culturing Vessel>

Figure 1B:
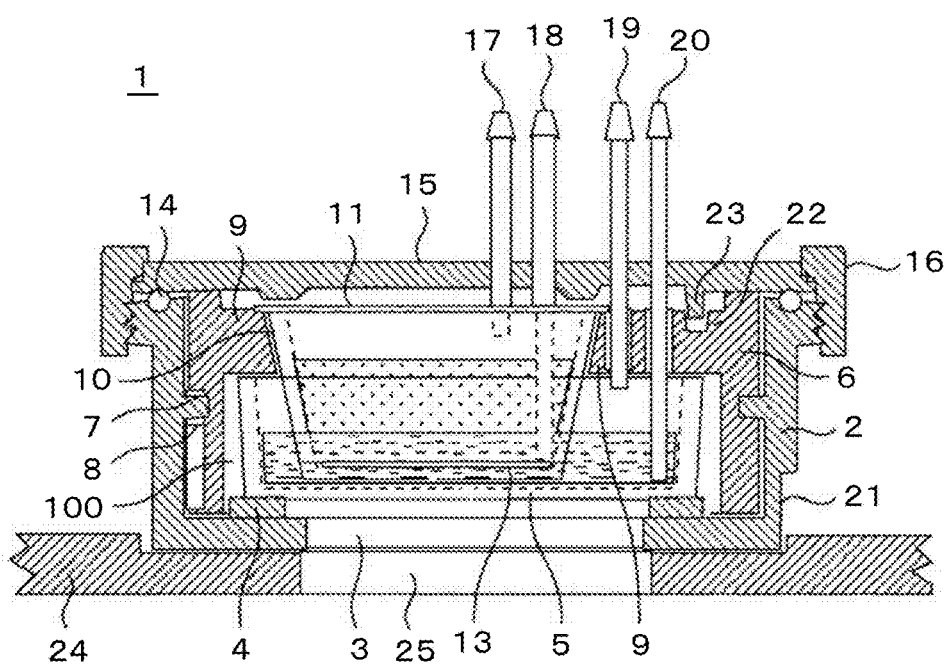
FIG. 1B shows a B-B' cross-section of FIG. 1A.
Figure 2A:
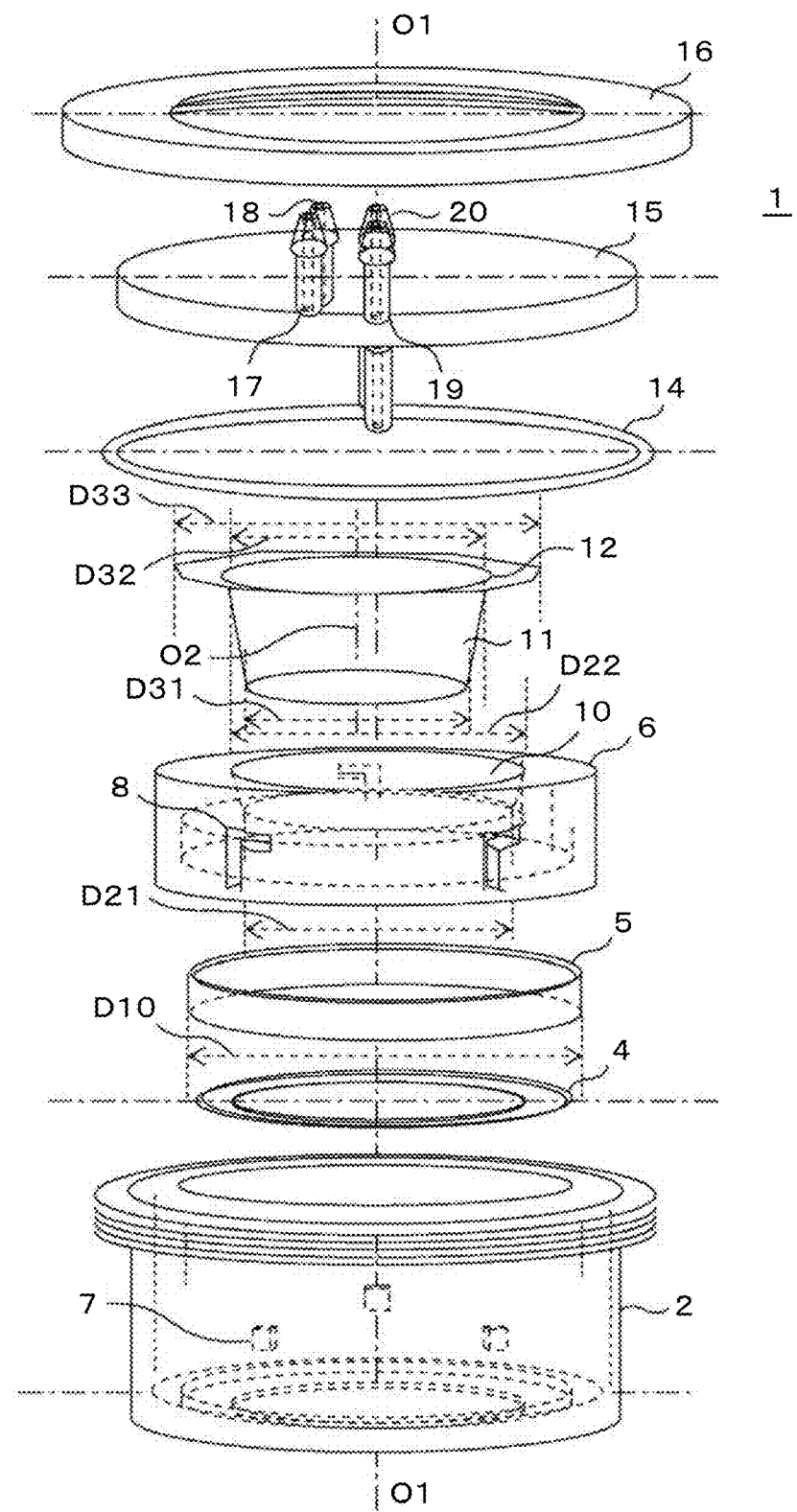
FIG. 2A is an exploded view of the cell culturing vessel of First Example.
Figure 2B:
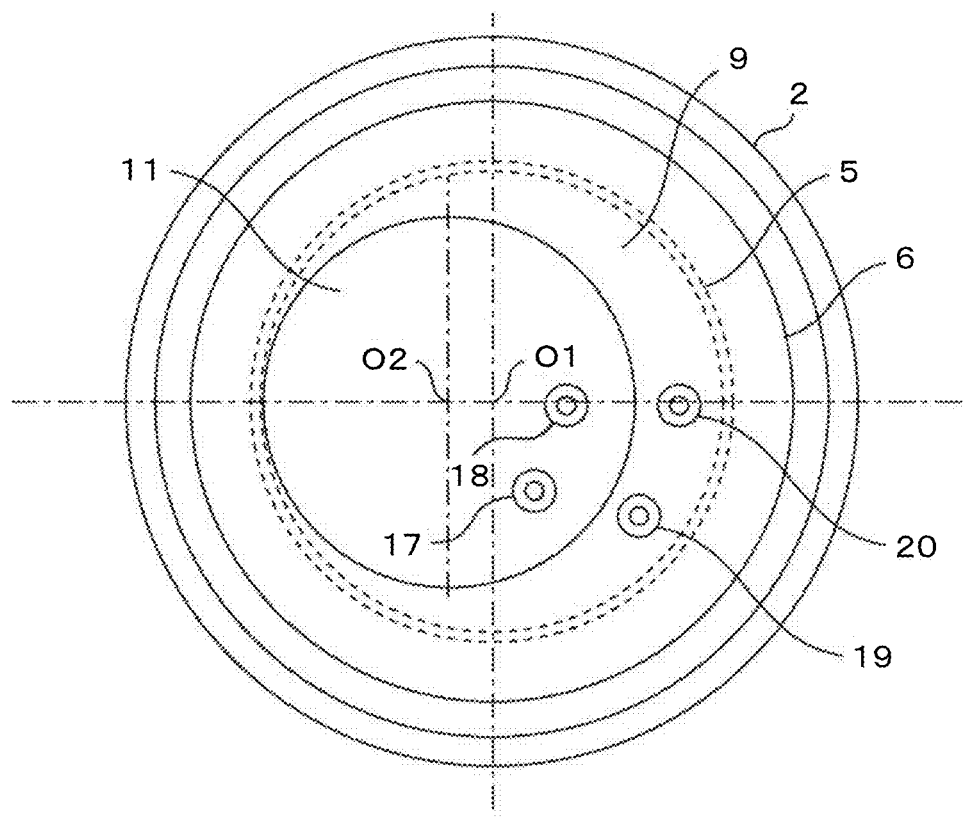
FIG. 2B is a view for describing the mutual relationship among components of the cell culturing vessel of First Example.

FIGS. 1A and 1B show the structure of the cell culturing vessel of First Example. FIG. 1A is a plan view and FIG. 1B shows the B-B' cross-section of FIG. 1A. FIG. 2A is an exploded view of the cell culturing vessel of First Example. FIG. 2B is a view for describing the mutual relationship among components of the cell culturing vessel.

A cell culturing vessel 1 has a main vessel 2, a pressing member 6, and a lid member 15. It is, as a whole, a vessel having almost a cylindrical profile. It is made of a plastic having both plasticity and rigidity such as polycarbonate (which will hereinafter be abbreviated as "PC"), polystyrene (which will hereinafter be abbreviated as "PS"), or polypropylene (which will hereinafter be abbreviated as "PP"). The main vessel 2 has a function of housing therein a first vessel and a second vessel. It is made by injection molding or the like and has an opening portion 3 at the bottom surface thereof. A rubber sheet (first elastic body) 4 in a ring form is placed adjacent to this opening portion 3 and a culture dish (the above-mentioned first vessel) 5 is placed in the main vessel 2 via the rubber sheet 4. This culture dish 5 is made of a plastic having both plasticity and rigidity such as PC or PS and can hold a culture medium having cells suspended therein. The culture dish may be made of a glass material according to the purpose of use. As the culture dish 5, any one as long as it is commercially available can be used. Examples include culture dishes manufactured by BD, Corning Inc., or Greiner Bio-one and no limitation is imposed on usable culture dishes. The inside bottom surface of the culture dish 5 has been subjected to surface treatment such as hydrophilicity imparting surface treatment for securing cell adhesion performance, which enables culture and growth of adhesive cells and the like.

FIGS. 1A and 1B show the main vessel 2 and the culture dish 5 which have already been fixed. The pressing member 6 has a cylindrical shape and has a hollow node portion 9. This means that this node portion 9 is provided with a through-hole 10 of an inverse truncated conical shape in which an insert vessel (the above-mentioned second vessel) 11 having an inverse truncated conical profile is to be inserted. The node portion 9 is in contact with, at the lower surface thereof, the circumferential upper edge of the culture dish 5. This pressing member 6 is fitted in and semi-fixed detachably to the main vessel 2 along the inner circumference thereof from above the culture dish 5. Described specifically, fixing of the pressing member 6 to the main vessel 2 is completed when a fitting protrusion 7 provided on the inner cylindrical surface of the main vessel 2 engages with a stepped fitting groove 8 provided on an outer cylindrical surface of the pressing member 6 and by application of a slight rotation angle to between the pressing member 6 and the main vessel 2, the fitting protrusion 7 engages with the stepped portion of the fitting groove 8. At this time, the rubber sheet 4 located on the bottom surface of the culture dish 5 is sandwiched between the culture dish 5 and the pressing member 6 and undergoes elastic deformation by the pressure therebetween and the main vessel 2 and the culture dish 5 are airtightly sealed. When a rotation angle is applied to the semi-fixed pressing member 6 in a direction opposite to the above-mentioned direction, the pressing member 6 is detached from the main vessel 2. The positional relationship between the main vessel 2 and the pressing member 6 can be kept horizontal by three or more sets of the fitting protrusion 7 and the fitting groove 8. Alternatively, another means such as screwing may be used for fixing the pressing member 6 and the main vessel 2 horizontally and detachably.

In the cell culturing vessel 1, the culture dish 5 is exposed to the outside in a region facing to the opening portion 3 of the bottom surface of the main vessel 2.

The pressing member 6 can hold the culture dish 5 in an inner cylindrical space portion 100 below the node portion 9 and at the same time, can hold an insert vessel 11, which is the second vessel, on the upper flat surface of the node portion 9. The insert vessel 11 has, on the upper surface thereof, a flange portion 12 as shown in FIG. 1A and, on the bottom surface parallel to the flange portion 12, a substance permeable membrane 13. A culture medium having cells suspended therein can be held in this vessel 11. The insert vessel 11 is made of a plastic having both plasticity and rigidity such as PC, PS, or polyethylene terephthalate (which will hereinafter be abbreviated as "PET"). The substance permeable membrane 13 and the frame portion of the insert vessel 11 are manufactured by heat welding or ultrasonic welding. The substance permeable membrane 13 has an average pore size of preferably 0.4 μm as one example permitting passage of protein or the like but not permitting passage of cells. As the insert vessel 11, a commercially available one may be used. Examples include those manufactured by BD, Corning Inc., or Nunc. No limitation is imposed on usable insert vessels.

The lid member 15 of the cell culturing vessel 1 has a circular or substantially circular (which will hereinafter be called "circular", simply) planar shape and is provided with a first port (first duct for injection into insert vessel) 17 for supplying a culture medium to the insert vessel 11, a second port (second duct for discharge from insert vessel) 18 for discharging the culture medium from the insert vessel 11, a third port (third duct for injection into culture dish) 19 for supplying a culture medium to a culture dish 5, and a fourth port (fourth duct for discharging from culture dish) for discharging the culture medium from the culture dish 5. The first to the fourth ports are each a duct having rigidity and a through-hole passes through the lid member 15 from the upper surface (outer surface of the cell culturing vessel 1) to the lower surface (inner surface of the cell culture device 1) thereof. The first to the fourth ports all extend in a direction perpendicular to the surface of the lid member 15, that is, in a perpendicular direction that coincides with an axis passing through the center of the cell culturing vessel (first vessel) 1.

In FIG. 1A, O1 means the center of the cell culturing vessel 1 (main vessel 2, pressing member 6, and lid member 15) and O2 means the center of the insert vessel 11. This means that the insert vessel 11 is eccentrically placed in the cell culturing vessel 1. The planar shape of the cell culturing vessel 1 or insert vessel 11 is not limited to a circular shape. When these vessels have a shape other than circle such as regular hexagon or ellipse, they may also be placed eccentrically while designating the centers of their shapes as O1 and O2, respectively.

The first port 17 is placed so that in the cell vessel 1, the opening end thereof comes slightly below the upper end of the insert vessel 11. The second port 18 is placed so that it comes close to the height of the substance permeable membrane 13 of the insert vessel 11 and at the same time, the opening end of it comes close to the vicinity of the outer peripheral position of the substance permeable membrane 13. The third port 19 is placed so that the opening end thereof comes slightly below the upper end of the culture dish 5. The fourth port 20 is placed so that it comes close to the height of the inside bottom surface of the culture dish 5 and at the same time, the opening end of it is placed at a position near the outer edge inside the culture dish 5. In addition, the first port 17 and the second port 18 to be connected to the insert vessel 11 are both placed on one side of the center O2 of the insert vessel 11 (in a region on the right side of O2 in FIG. 1A). The third port 19 and the fourth port 20 to be connected to the culture dish 5 are both placed on one side of the center O1 of the culture dish 5 and at the same time, on the same side as the first port 17 and the second port 18 (in a region on the right side of O1 in FIG. 1A). This means that the first to fourth ports are all placed on the same side of the cell culturing vessel 1 (culture dish 5) with respect to the center O1 and at the same time, in a region on the side opposite to the center O2 of the insert vessel 11.

In particular, the second port 18 and the fourth port 20 are placed on the same side when viewed from the circle center (O1) of the culture dish 5 or from the circle center (O2) of the insert vessel 11 and at the same time, on the same straight line in a radius direction.

The lid member 15 is fixed to the main vessel 2 via an O ring (second elastic body) 14. The outer circumference of the lid member 15 has a stepped structure having an upper portion and a lower portion in which the lower portion has an outer diameter greater than that of the upper portion. The main vessel 2 has, at the upper portion thereof, a predetermined O ring groove capable of holding the O ring therein and the O ring 14 is housed in this O ring groove while exposing the contact surface with the lid member 15. The main vessel 2 has a male screw outside the O ring groove and it is screwed in a female screw provided in a lid fixing ring 16. The lid fixing ring 16 has, at the center thereof, an opening portion and it has an inner diameter corresponding to the outer diameter of the stepped structure at the outer circumference of the lid member 15. The lid member is fixed to the main vessel 2 by placing the lid member 15 at the upper-surface opening portion of the main vessel 2 of the cell culturing vessel 1 via the O ring and fixing the lid fixing ring 16 to a screw portion at the outer circumference of the main vessel 2 with a screw. An inner space defined by the lid member 15 and the main vessel 2 except for the first port 17 to the fourth port 20 is therefore airtightly sealed. Further, they are fixed with a screw so that even when the lid member 15 is detached from the main vessel 2 in a horizontal state, almost no external force is applied to a culture medium in the main vessel 2.

As shown in FIG. 2A which is an exploded view of the cell culturing vessel 1, the main vessel 2, the rubber sheet 4, the culture dish 5, the pressing member 6, the O ring 14, the lid member 15, and the lid fixing ring 16 each have a circular shape and the centers of these circles are placed in series along a height-direction axis O1-O1. Assuming that the diameter (inner diameter) of the culture dish 5 is represented by D10, the diameter of the lower surface of the through-hole of the node portion 9 of the pressing member 6 is represented by D21, the diameter of the upper surface of the through-hole of the node portion 9 is represented by D22, the diameter (outer diameter) of the bottom surface of the insert vessel 11 is represented by D31, the diameter (outer diameter) of the upper opening of the insert vessel 11 is represented by D32, and the length of the long axis of the flange portion 12 is represented by D33, they satisfy the following equations:

$$D10>D21, D21>D31, D32>D31, D22>D32, D33>D22$$

This means that the inner diameter D10 of the culture dish 5, the diameter D21 of the lower surface of the through-hole (the diameter of the through-hole unless particular discrimination is necessary), and the diameter D31 of the bottom surface of the insert vessel 11 (the diameter of the insert vessel unless particular discrimination is necessary) satisfy the following equation:

$$D10>D21>D31$$

It is to be noted that the center (O2) of the insert vessel 11 is placed from 2 to 3 mm eccentrically placed to the center axis O1-O1 of the other parts (the culture dish 5 and the pressing member 6). This eccentricity has an advantage which will be described later.

In an internal space 100 of the cell culturing vessel 1, the insert vessel 11 passes through the through-hole 10 provided at the node portion 9 of the pressing member 6 and it has a bottom surface contiguous to the inside bottom surface of the culture dish 5. The lower and upper surfaces of the node portion 9 of the pressing member 6 are parallel to each other. The circumferential upper edge of the culture dish 5 contiguous to the lower surface of the node portion 9 is also parallel to the above-mentioned inside bottom surface of the culture dish 5 and in addition, the flange portion 12 of the insert vessel 11 contiguous parallel to the upper surface of the node portion 9 of the pressing member 6 and the substance permeable membrane 13 of the insert vessel 11 are parallel so that the inside bottom surface of the culture dish 5 and the substance permeable membrane 13 are in a parallel positional relationship. The distance of these two parallel culture surfaces is defined by a perpendicular distance of the node portion 9 of the pressing member 6 between a contact to the culture dish 5 and a contact to the flange portion 12. Assuming that the height from the inside bottom surface of the culture dish 5 to the upper surface of the culture dish 5 is represented by H1, the distance (the above-mentioned perpendicular distance) of the node portion 9 of the pressing member 6 between the lower surface and the upper surface is represented by H2, the height from the bottom surface of the insert vessel 11 to the flange 12 is represented by H3, and the height from the bottom surface of the insert vessel 11 to the inside bottom of the culture dish 5 is represented by H4, they satisfy the following equation:

$$H1+H2 \approx H3+H4$$

This means that H1+H2 and H3+H4 are equal or substantially equal.

In the present example, the distance (perpendicular distance H2) between two culture surfaces is set at 0.9 mm. This distance is however one example and the optimum perpendicular distance may be selected also in consideration of a liquid amount of a culture medium so as to keep the liquid surface of the culture medium which has filled the lower culture dish at a position contiguous to the substance permeable membrane 13 and as high as possible.

The main vessel 2 has, in the vicinity of the bottom surface thereof, one or more positioning grooves 21. The pressing member 6 has a positioning hole 22. The lid member 15 has, at the lower surface thereof, a positioning pin 23 that engages with the positioning hole 22. The cell culturing vessel 1 of the present example is placed in a recess of a stage 24 and the cell culturing vessel 1 of the present example is placed so as to engage with the bottom shape of the main vessel 2. The stage 24 has, at the center of the recess thereof, an observation opening portion 25. Since the stage 24 has a positioning protrusion that engages with the positioning groove 21 of the main vessel 24, the direction from the center of the main vessel 2 to the stage 24 is known. Since the fitting protrusion 7 engages with the fitting groove 8, the direction from the center of the pressing member 6 is known. Further, since the positioning pin 23 of the lid member 15 fits in the positioning hole 22 of the pressing member 6, the direction from the center of the lid member 15 is known. The direction of the second port 18 and the fourth port 20 provided in the lid from the center to the stage 24 is therefore known.

As described above as the third problem, in cell culture having two culture layers, contamination of cells to be cultured in the lower layer with cells to be cultured in the upper layer should be prevented. In particular, splash containing feeder cells generated during cell seeding may attach to the inside of the insert vessel which is an upper-layer vessel. In First Example, the diameter D21 of the lower portion of the through-hole 10 which the node portion 9 has is smaller than the inner diameter D10 of the culture dish 5 and greater than the outer diameter D21 of the bottom surface of the insert vessel 11 so that the node portion 9 acts as a side wall covering, from above, the opening surface of the culture dish 5 located outside of the insert vessel 11. This makes it possible to prevent splash, which has been generated during seeding of a feeder cell liquid from the third port 19 to the culture dish 5, from reaching the inside of the insert vessel 11, blocked by the node member 9 serving as a barrier.

<Cell Culturing Vessel and Constitution of Automatic Cell Culturing Device>

Figure 3:
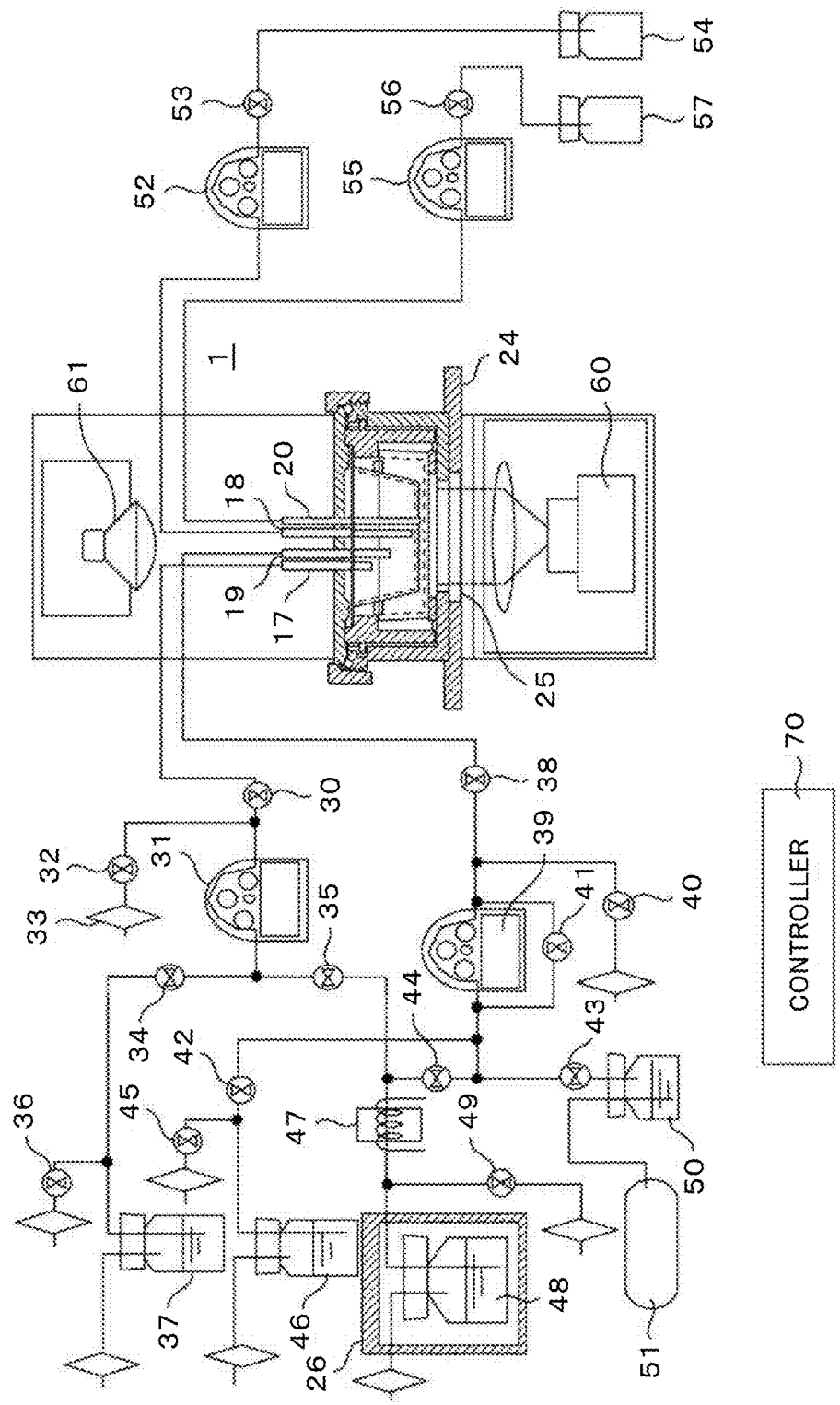
FIG. 3 is a view showing the constitution of the cell culturing device of First Example including one cell culturing vessel, a liquid delivery unit, and a cell observation unit.

FIG. 3 shows one example of an automatic cell culturing device using the cell culturing vessel of First Example. More specifically, FIG. 3 shows the relationship, in an automatic cell culturing device having the cell culturing vessel 1 and a liquid delivery control unit for controlling supply or discharge of a culture medium to or from the cell culturing vessel, between a liquid and gas delivery method and an observation unit. The cell culturing vessel 1 should be maintained at a culturing temperature most suited for cell culture and components of the cell culturing vessel 1 shown in FIG. 3 is set in a constant temperature bath not shown. In the present example, there are two cases, that is, a cell-containing medium is delivered to the cell culturing vessel 1 and only a culture medium is discharged or delivered from or to the vessel. Liquid delivery and gas delivery to the cell culturing vessel 1 may be performed by making use of a liquid delivery flow channel commonly.

To the first port 17 of the cell culturing vessel 1, a first vessel open/close valve 30 of the liquid delivery control unit is connected through a rubber tube. The upstream of the valve is divided into two streams. One is connected to a first pump 31, while the other one is connected to a first exhaust open/close valve 32 and upstream thereof, to a filter 32. The other connection port of the filter is opened to the air. As a valve mechanism to be used for these first vessel open/close valve 30 and the first exhaust open/close valve 32, an electromagnetic valve is suited. A so-called electromagnetic valve operates through a mechanism in which a rubber tube is inserted (connected) in a part that opens/closes by the action of an electromagnet and the electromagnetic valve is turned ON/OFF to cause elastic deformation to narrow or open the tube portion. The term "valve" will hereinafter mean an "electromagnetic valve". A pump to be used as the first pump 31 is preferably a typical roller pump. A so-called roller pump operates through a mechanism that an internal gas or liquid is delivered by rotating a motor to cause elastic deformation of a rubber tube wound (connected) around a roller attached to the shaft of the motor. The term "pump" will hereinafter mean a roller pump. A filter 33 takes a gas from the outside of the flow channel to control the atmospheric pressure inside the flow channel and, for example, a filter that does not allow passage of particles having a particle size of 0.22 μm or greater is used. The term "filter" will hereinafter mean a filter of the same quality.

The upstream of the first pump 31 is divided into two streams. One is connected to a first cell open/close valve 34 and the other one is connected to a first medium switching valve 35. The upstream of the first cell open/close valve 34 is divided into two streams. One is connected to a first cell pressure reducing valve 36 and upstream thereof, connected to a filter, while the other one is connected to a first cell liquid 37. The first cell liquid 37 in a cell bag contains cells to be cultured. The cells are retained while being suspended in a culture medium. The cell bag for retaining therein the first cell liquid 37 is provided with an introduction tube and a filter for controlling the atmospheric pressure in the bag.

To the third port 19 of the cell culturing vessel 1, a second vessel open/close valve 38 is connected through a rubber tube and the upstream of the valve is divided into two streams. One is connected in a direction of a second pump 39 and the other one is connected to a second exhaust open/close valve 40 and upstream thereof, connected to a filter. The other connection port of the filter is opened to the air. The upstream and downstream of the second pump 39 are each divided into two streams and they are connected to each other so as to by-pass the second pump 39. A second gas open/close valve 41 is connected between them.

The upstream of the second pump 39 is divided into two streams. One is connected to a second cell open valve 42. The other one is divided again into two streams and one is connected to a first gas open/close valve 43 and the other one is connected to a second medium switching valve 44.

The upstream of the second cell open valve 42 is divided into two streams. One is connected to a second cell pressure reducing valve 45 and upstream thereof, connected to a filter. The other one is connected to a second cell liquid 46. The second cell liquid 46 in a cell bag contains cells to be cultured. These cells are retained while being suspended in a culture medium. The cell bag for retaining therein the second cell liquid 46 is provided with an introduction tube and a filter for controlling the atmospheric pressure in the bag.

Both the first medium switching valve 35 and the second medium switching valve 44 are, upstream thereof, connected to a preheating mechanism 47. The upstream of it is divided into two streams and they are connected to a culture medium 48 and a liquid medium pressure reducing valve 49, respectively. With regard to the culture medium 48, a culture medium is retained in a cell bag and the culture medium is refrigerated in a refrigerator 26. At the time of cell culture, cells during a culturing procedure are kept at 37° C. The culture medium can be added to the cell culturing vessel 1 after heating by allowing it to pass through the preheating mechanism 47, because direct addition of a refrigerated culture medium destabilizes cell growth.

The above-mentioned first gas open/close valve 43 is, upstream thereof, connected to a humidification bottle 50. The humidification bottle 50 is, upstream thereof, connected to a carbon dioxide bottle 51 pressurized at an optimum concentration. In order to prevent the culture medium during cell culture from undergoing a time-dependent pH change, gas exchange from the surface of the liquid medium with a carbon dioxide gas should be performed periodically. Further, concentration of a culture medium component due to evaporation of the culture medium should be prevented. The carbon dioxide gas introduced from the bottle 51 is humidified to an optimum humidity in the humidifying bottle and then is made to wait.

The second port 18 of the cell culturing vessel is connected to a fourth pump 52 through a rubber tube. The fourth pump is, downstream thereof, connected to a fourth vessel open/close valve 53. The vale is, downstream thereof, connected to an upper-layer waste-liquid bottle 54. The fourth port 20 is connected to a third pump 55 through a rubber tube. The third pump is, downstream thereof, connected to a third vessel open/close valve 56. The valve is, downstream thereof, connected to a lower-layer waste-liquid bottle 57.

A microscopic observation unit 60 is placed below an observation opening portion 25 of the stage 24 having the cell culturing vessel 1 thereon. On the other hand, a light irradiation portion 61 which is a part of the microscopic observation unit is placed above the first to fourth ports of the cell culturing vessel 1. The perpendicular position and tilt angle of the stage 24 relative to the microscopic observation unit 60 can be adjusted by using an up/down drive device (not illustrated).

In FIG. 3, the observation opening portion 25 is greater than the outer diameter of the substance permeable membrane 13 of the insert vessel 11 and it has an observation range equal to or greater than the bottom surface of the insert vessel 11. Further, in the present example, the first port 17, the second port 18, the third port 19, and the fourth port 29 connected to the cell culturing vessel 1 are placed only in a region on one side of the center 02 of the insert vessel 11, for example, in a right-half region as shown in FIGS. 1B and 2B, further in a right half region of the center 01 of the culture dish 5. This means that in more than half of the region of the cells to be observed including the other region (for example, a left-half region of O2 in FIGS. 1B and 2B), flow channels and rubber tubes are not placed so that more than half of the observation visual field can be ensured.

A controller 70 uses a computer and based on its program, it allows the computer to achieve a function of totally controlling an automatic cell culturing device, such as controlling ON/OFF of a liquid delivery control unit such as pump or electromagnetic valve. In other words, the controller controls liquid delivery/discharge and gas delivery/discharge to/from the cell culturing vessel 1 via the first to fourth ports and at the same time, supports an operator in observing cells in the cell culturing vessel 1.

<Cell Culture Operation, Observation Operation>

Figure 4A:
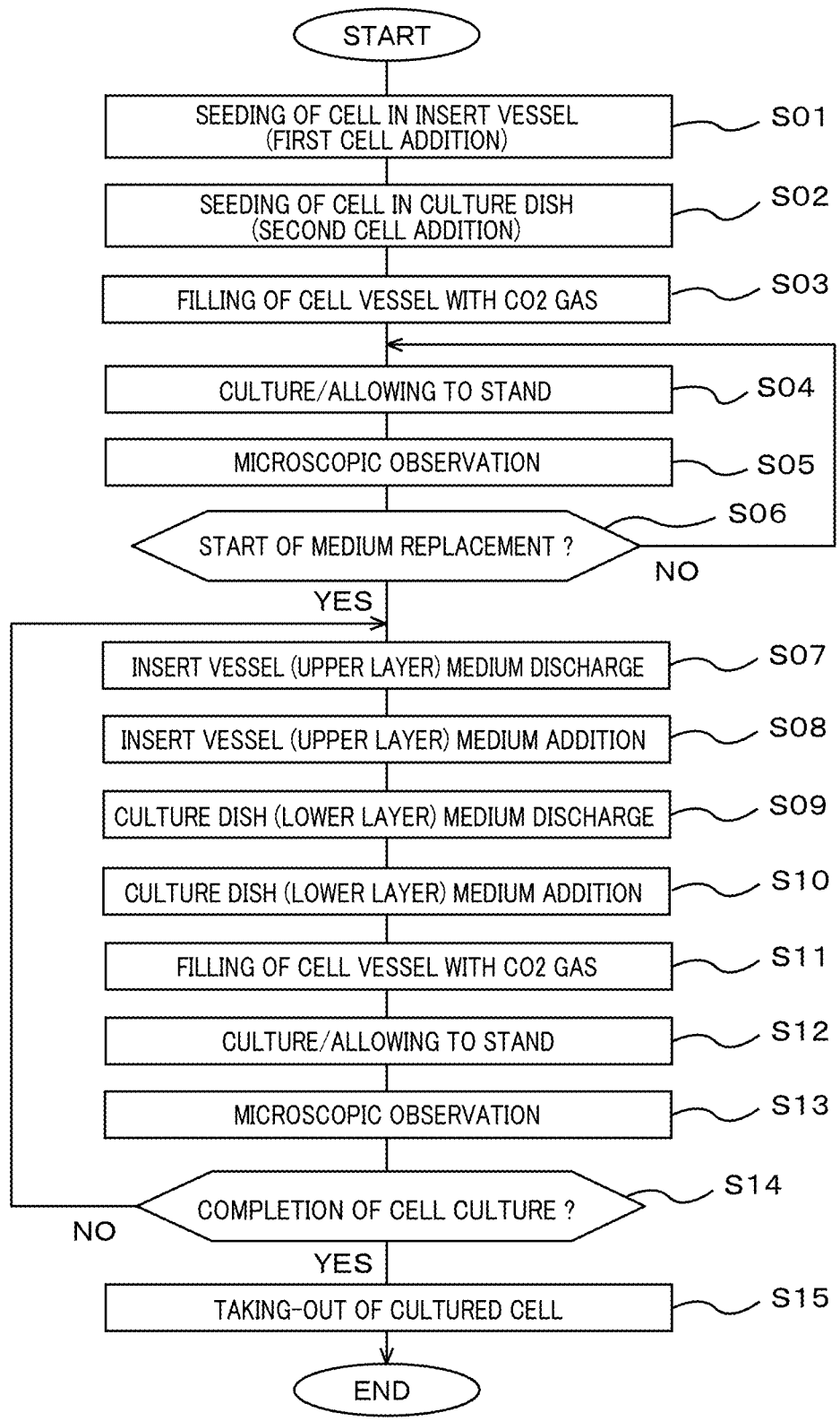
FIG. 4A is a flow chart of cell culture operation and observation operation in the cell culturing device of First Example.

FIG. 4A is a flow chart of overall operations controlled by the controller 70 such as cell culturing and observation in the cell culturing device. First, cells are seeded (first cell addition) in the insert vessel 11 of the cell culturing vessel 1 (S01) and then, cells are seeded (second cell addition) in the culture dish 5 (S02). After filling the cell culturing device with a $CO_2$ gas (S03), the cells are cultured and allowed to stand (S04). Then, the cultured cells are observed using a microscope (S05), followed by determination whether medium replacement is started or not (S06). In medium replacement, insert vessel (upper layer) medium discharge (S07), insert vessel (upper layer) medium addition (S08), culture dish (lower layer) medium discharge (S09), and culture dish (lower layer) medium addition (S10) are performed. After filling the cell culturing vessel with a $CO_2$ gas (S11), the cells are cultured and allowed to stand (S12). Then, the cultured cells are observed using a microscope (S13), followed by determination whether cell culture is completed or not (S14). After completion of the cell culture, the cultured cells are taken out (S15).

Figure 4B:
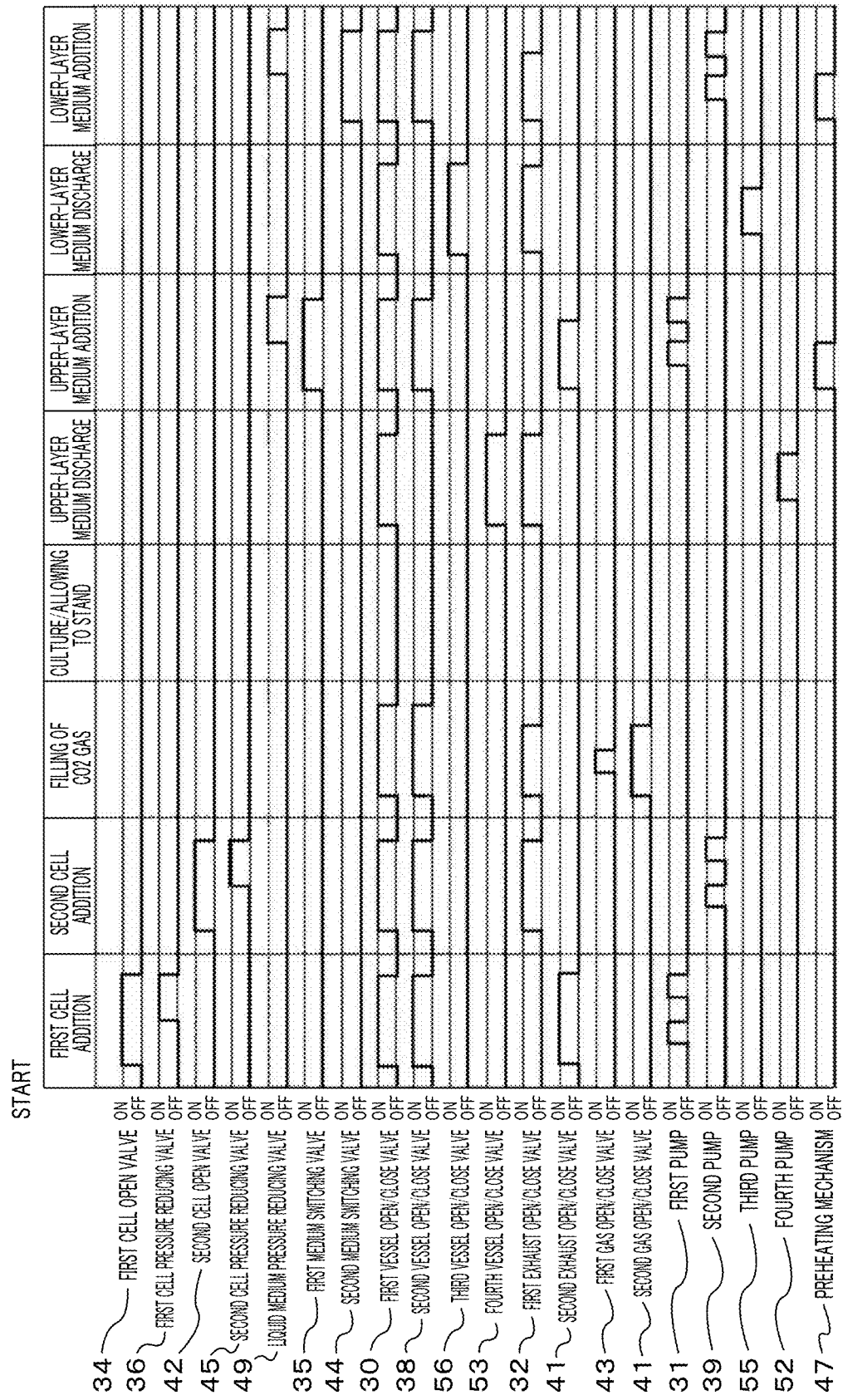
FIG. 4B is an operation time chart in cell culture using the cell culturing device of First Example.

FIG. 4B is a time chart of liquid delivery/gas delivery in the cell culturing vessel 1 to be controlled by the controller 70. The operation item and time axis are shown along the abscissa direction, while the operation timing of the electromagnetic valves and the pumps clearly shown in FIG. 3 including those from the first cell open/close valve 34 to the fourth pump 52 are shown along the ordinate direction. In the initial state, all the valves are turned OFF so that they are closed and all the pumps are turned OFF, meaning that liquid delivery is stopped.

Cells are seeded in the insert vessel 11 in the cell culturing vessel 1 (S01 in FIG. 4A) based on the first cell addition operation. By turning the first cell open/close valve 34, the second vessel open/close valve 38, the first vessel open/close valve 30, and the exhaust open/close valve 41, which are in an initial state, ON to open these valves, a flow channel communicates between the first cell liquid 37 and the first port 17 through the first cell pressure reducing valve 34 and the first vessel open/close valve 30. Further, a filter communicating with the outside air communicates with the second exhaust open/close valve 40 and the second vessel open/close valve 38 and a flow channel leads to the third port 19 from a filter connected to the second exhaust open/close valve 40. Then, by turning the first pump 31 ON for a predetermined time, a cell liquid is delivered from the first cell liquid 37, passes through the first port 17, and reaches the insert vessel 11. Although the cell vessel 1 is hermetically sealed, the flow channel from the third port 19 to the filter communicating with the outside air is opened so that the atmospheric pressure in the insert vessel 11 and the culture dish 5, each in the cell vessel 1, is adjusted to an appropriate value. Then, when the first pump 31 is turned OFF for a predetermined time and then, the first cell pressure reducing valve 36 is turned ON to communicate the flow channel between the filter communicating with the outside air and the first cell liquid 37, the cell liquid in the middle of the channel (upstream side of the divided position) returns to the first cell liquid 37 and a node of the air is formed in this channel. By turning the first pump 31 for a predetermined time again, the cell liquid in the channel reaches the insert vessel 11 through the first port 17. After a predetermined amount is injected, each opened valve is turned off to close it.

Next, cells are seeded in the culture dish 5 (S02) based on the second cell addition operation. By turning the second cell open valve 42, the first vessel open/close valve 30, the second vessel open/close valve 38, and the first exhaust open/close valve 32, which are in an initial state, ON to open these valves, a flow channel communicates between the second cell liquid 46 to the third port 19 through the second vessel open/close valve 38. Further, a flow channel communicates between the filter 33 and the first port 17 through the first exhaust open/close valve 32 and the first vessel open/close valve 30. Then, by turning the second pump 39 ON for a predetermined time, a cell liquid is delivered from the second cell liquid 46, passes through the third port 19, and reaches the culture vessel 5. Although the cell vessel is hermetically sealed, the flow channel from the first port 17 to the filter 33 communicating with the outside air is opened so that the atmospheric pressure in the cell vessel is adjusted. Then, when the second pump 39 is turned OFF for a predetermined time and then, the second cell pressure-reducing valve 36 is turned ON to communicate the flow channel between a filter communicating with the outside air and the second cell liquid 45, the cell liquid in the middle of the flow channel (upstream side of the divided position) returns to the second cell liquid 46 and a node of the air is formed in this channel. By turning the second pump 39 ON for a predetermined time again, the cell liquid in the flow channel reaches the culture dish 5 through the third port 19. After a predetermined amount is injected, each opened valve is turned off to close it.

The cell culturing vessel 1 is filled with a $CO_2$ gas (S03) based on the $CO_2$ gas filling operation. By turning the first vessel open/close valve 30, the second vessel open/close valve 38, the second gas open/close valve 41, and the first exhaust open/close valve 32, which are in an initial state, ON to open each of these valves, a flow channel to the third port 19 is opened through the first gas open/close valve 43 and the second vessel open/close valve 38. In addition, a flow channel communicates between the filter 33 and the first port 17 through the first exhaust open/close valve 32 and the first vessel open/close valve 30. Then, by turning the first gas open/close valve 43 ON for a predetermined time, an optimally humidified $CO_2$ gas reaches, after passing through the second vessel open/close valve 38 and the third port 19, the cell vessel 1 from the bottle 51 through the humidification bottle 50. Although the cell vessel 1 is hermetically sealed, the flow channel from the first port 17 to the filter 33 communicating with the outside air is opened so that a $CO_2$ gas pressure inside the cell vessel is adjusted to atmospheric pressure. After injection of a predetermined amount of a $CO_2$ gas, each valve is turned OFF to close it.

Since the first cell liquid is retained in the insert vessel 11, the second cell liquid is retained in the culture dish 5, the space of the culturing vessel 1 is filled with an optimally humidified $CO_2$ gas, and the cell culturing vessel 1 is kept at an optimum temperature, cell culture is continued by allowing them to stand and thereby retaining them for a predetermined time (S04). Cells in the cell liquids proliferate while adhering to the upper portion of the substance permeable membrane 13 of the insert vessel 11 or the inner bottom surface of the culture dish 5 so that the culture medium whose components have changed with the progress of culture can be separated from the cells and discharged.

Cell observation (S05) during cell culture is performed using the microscopic observation unit 60 and the light irradiation member 61 during the operation of allowing the cell liquids to stand to culture them. An up/down drive device not illustrated but placed on the stage 24 can move the cell culturing vessel 1 up and down and thereby adjust the focal length to enable clearer observation of the cells through the microscopic observation unit 60. In the present example, the microscopic observation is performed using a phase contrast microscope but it may be replaced by an inverted-type optical microscope or the like.

Figure 6:
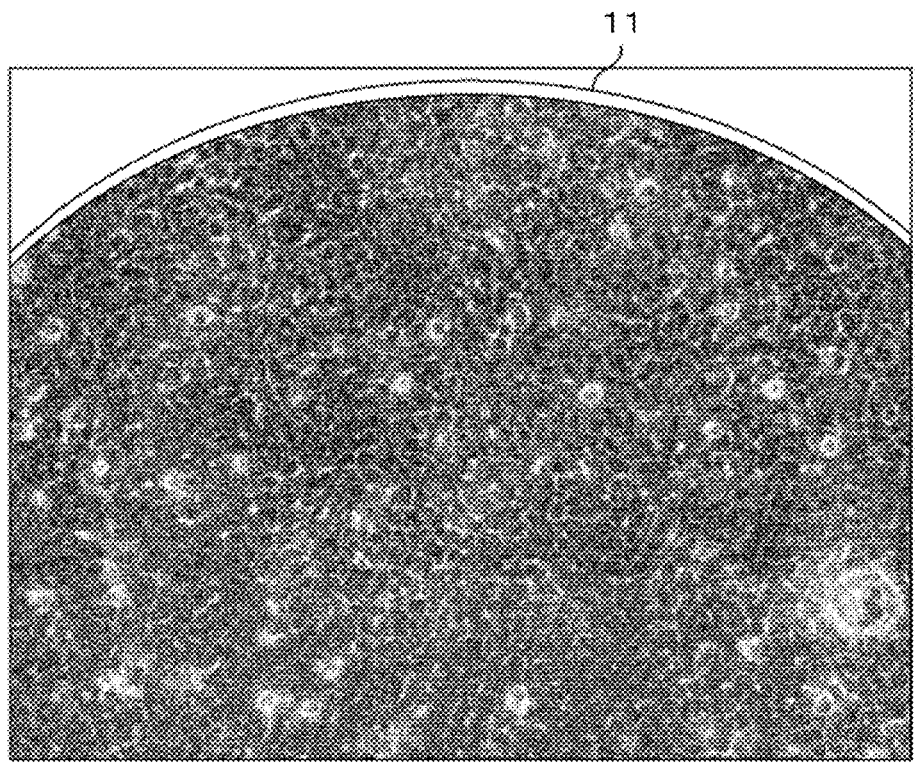
FIG. 6 is a view showing one example of cell observation results in First Example.

FIG. 6 shows one example of the observation results of cells on the insert vessel 11 obtained by a culture test using the cell culturing vessel in the present example. The related art has, as the problem thereof, low transparency of a culturing vessel itself to prevent clear observation. The observation results of the present example show that cells cultured in the insert vessel can be observed clearly. The culture dish 5 is placed nearer to the microscopic observation unit 60 than the insert vessel 11 and cells on the culture dish 5 can also be observed clearly. This means that even when cells to be observed are different in focal position from the microscope in double-layer culture, adjustment of a focal length as needed by the up/down drive device of the cell culturing vessel 1 enables clear observation of a plurality of cells during culturing.

Next, medium replacement (S06) in the cell culturing vessel 1 is performed based on the upper-layer medium discharge, upper-layer medium addition, lower-layer medium discharge, and lower-layer medium addition operations described in the operation time chart shown in FIG. 4B. In the upper-layer medium discharge operation (S07), when the first vessel open/close valve 30, the first exhaust open/close valve 32, and the fourth vessel open/close valve 53, which are in an initial state, are turned ON to, open each of the valves, a flow channel communicates between the second port 18 and the upper-layer discharge bottle 54 through the fourth vessel open/close valve 53. In addition, a flow channel communicates between the filter 33 to the first port 17 through the first exhaust open/close valve 32 and the first vessel open/close valve 30. Next, when the fourth pump 52 is turned ON for a predetermined time, the cell liquid is suctioned from the insert vessel 11 and the culture medium reaches the upper-layer discharge bottle 54. Although the cell culturing vessel 1 is hermetically sealed, the flow channel from the first port 17 to the filter 33 communicating with the outside air is opened so that atmospheric pressure inside the cell culturing vessel is adjusted. After suction of a predetermined amount of the culture medium is completed, each opened valve is turned OFF to close it.

A culture medium is added to the insert vessel 11 (808) based on the upper-layer medium addition operation. By turning the first medium switching valve 35, the first vessel open/close valve 30, the second vessel open/close valve 38, and the second exhaust open/close valve 40, which are in an initial state, ON to open these valves and turning the preheating mechanism 47 ON, a flow channel communicates between the culture medium 48 and the first port 17 through the preheating mechanism 47, the first medium switching valve 35, and the first vessel open/close valve 30. Further, a flow channel communicates between the filter to the third port 19 through the second exhaust open/close valve 40 and the second vessel open/close valve 38. Next, by turning the first pump 31 ON for a predetermined time, a culture medium is delivered from the culture medium 48, while the cell liquid reaches the insert vessel 11 through the first port 17. Although the cell vessel is hermetically sealed, the atmospheric pressure inside the cell vessel is adjusted because a flow channel from the third port 19 to the filter communicating with the outside air is opened. Next, when the first pump 31 is turned OFF after a predetermined time and the liquid medium pressure reducing valve 49 is turned ON to communicate a flow channel between the filter communicating with the outside air and the culture medium 48, the culture medium in the middle of the flow channel (upstream side of the divided position) returns to the culture medium 48 and a node of air is formed in the channel. By turning the first pump 31 ON for a predetermined time again, the culture medium in the flow channel reaches the insert vessel 11 through the first port 17. After a predetermined amount is injected, each opened valve is turned off to close it.

In lower-layer medium discharge operation (S09), when, the first vessel open/close valve 30, the first exhaust open/close valve 32, and the third vessel open/close valve 56, which are in an initial state, are turned ON to open these valves, a flow channel communicates between the fourth port 20 and the lower-layer discharge bottle 57 through the third vessel open/close valve 56. Further, a flow channel communicates between the filter 33 and the first port 17 through the first exhaust open/close valve 32 and the first vessel open/close valve 30. Next, by turning the third pump 55 ON for a predetermined time, the cell liquid is suctioned from the culture dish 5 and the culture medium reaches the lower-layer discharge bottle 57, passing through the fourth port 20. Although the cell culturing vessel 1 is hermetically sealed, the atmospheric pressure inside the cell culturing vessel is adjusted because a flow channel from the first port 7 to the filter communicating with the outside air is opened. After completion of suction of a predetermined amount of the culture medium, each opened valve is turned OFF to close it.

Next, a culture medium is added (S10) to the culture dish 5 based on the lower-layer medium addition operation. By turning the second medium switching valve 44, the first vessel open/close valve 30, the second vessel open/close valve 38, and the first exhaust open/close valve 32, which are in an initial state, ON to open these valves and turning the preheating mechanism ON, a flow channel communicates between the culture medium 48 and the third port 19 through the second medium switching valve 44 and second vessel open/close valve 38. Further, a flow channel communicates between the filter 33 and the first port 17 through the first exhaust open/close valve 32 and first vessel open/close valve 30. Next, by turning the second pump 39 ON for a predetermined time, the culture medium is delivered from the culture medium 48 and the cell liquid reaches the culture dish 5, passing through the third port 19. Although the cell vessel is hermetically sealed, the atmospheric pressure inside the cell vessel is adjusted because a flow channel from the first port 17 to the filter communicating with the outside air is opened. Next, when the second pump 39 is turned OFF for a predetermined time and the liquid medium pressure-reducing valve 49 is turned ON to communicate between the filter communicating with the outside air and the culture medium 48, the culture medium in the middle of the flow channel returns to the culture medium 48 and a node of air is formed in the flow channel. By turning the second pump 39 ON for a predetermined time again, the culture medium in the flow channel reaches the culture dish 5 through the third port 19. After a predetermined amount is injected, each opened valve is turned off to close it.

Next, the cell culturing vessel 1 is filled with the air so that the $CO_2$ gas filling operation (S11) is performed as described above in order to fill the vessel with a $CO_2$ gas.

Figure 5:
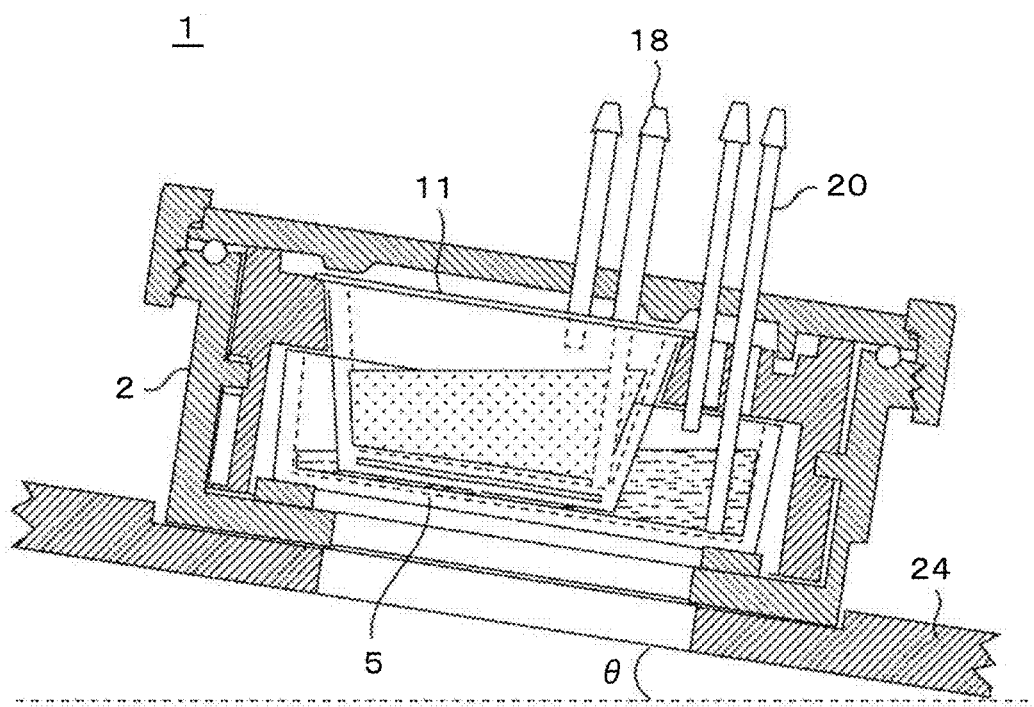
FIG. 5 is a view showing a discharging method of a culture medium in First Example.

In the upper-layer medium discharge and lower-layer medium discharge operations, the culture medium which has undergone a component change should be discharged as much as possible so as not to leave the medium in each vessel. FIG. 5 shows the state of the cell culturing vessel 1 during medium discharge. More specifically, the cell culturing vessel 1 is placed on the stage 24 so as to fit therein and it is tilted at an angle θ of 10 degrees by an up/down drive device not illustrated in this drawing. Since the direction from the center of the second port 18 and the fourth port 20 to the stage 24 is known, the up/down drive control can be performed easily. In the state shown in FIG. 5, the second port 18 and the fourth port 20 are tilted to reach the lowest point of the insert vessel 11 and the lowest point of the culture dish 5, respectively, the culture media to be replaced gather at the respective lowest points of the vessels, facilitating discharge of them by suction. The tilt angle θ of the cell culturing vessel 1 is not limited. By regulating the operation timing of the up/down drive device and the third pump 55 or the fourth pump 52 as needed, the culture medium can be discharged by the most suited method, for example, by suctioning the medium while tilting the cell vessel successively from the horizontal direction to the intended angle θ or decreasing the suction rate at the start time of the discharge and increasing it at the end time.

In addition, in the present example, the center 02 of the insert vessel 11 is eccentric to the center 01 of the culture dish 5 and a distance between the outside wall of the insert vessel 11 and the inside wall of the culture dish 5 is not uniform. At the time of the culture medium discharge operation from the culture dish 5, surface tension of a culture medium between the outside wall of the insert vessel 11 and the inside wall of the culture dish 5 becomes maximum along the outer circumferential circle when they are circles having the same center. In the present example, they are eccentric to each other so that the surface tension is small which is effective for lessening the remaining amount of the culture medium at the time of the culture medium discharge operation.

The up/down drive mechanism provided on the stage 24 has a function of tilting the cell culturing vessel and can give the lowest point everywhere in a horizontal direction. By tilting the vessel continuously, the liquid retained in the cell vessel is caused to flow along the outer circumference and thus a rotational movement (which will hereinafter be called "rotation movement") can be caused. In the cell seeding operation, cells should be cultured at regular intervals while being fixed on the bottom surface of the culture dish or insert vessel. In manual operation, the cell dishes are shaken and uniform distribution of cells is confirmed through macroscopic observation. In the present example, however, rotation movement is given to the cell-containing medium by operating the up/down drive mechanism after the above-mentioned cell seeding operation.

Further, in First Example, the center of the insert vessel 11 and the center of the culture dish 5 are eccentric to each other and the volume of the culture dish 5 from the center to the circumference of the inside wall is not uniform due to the presence of the outside wall of the insert vessel. When rotation movement is given to the culture medium in the cell seeding operation in the culture dish 5, rotation movement, which is originally uniform, is disturbed by the presence of the insert vessel 11. The culture medium is therefore stirred while being rotated so that the cells can be fixed at more regular intervals.

In automated cell culture, the cell culture operation (S12) is required to have a function of often monitoring the state of cells, observing the culture state and recording the observation results, and changing a cell culturing process as needed. In the present example, after seeding, whether cells have been seeded at an appropriate interval or not can be confirmed based on the microscopic observation results (S13). When it is found that the interval between cells is not an appropriate, rotation movement is added further to the cell vessel to achieve more uniform and more stable cell culture.

As described above, in the present example, the first to fourth ports are all placed on one side of the center of the first vessel so that flow channels and rubber tubes are placed in a region on one side of the cell culturing vessel 1 and in the other region, placement of the flow channels and rubber tubes is avoided. This ensures more than half of an observation visual field in macroscopic observation. FIG. 6 shows that in the upper portion of this drawing, a portion of the vessel and cells are both recorded on an observation image, suggesting a wide observation visual field.

<Overall View of Cell Culturing Device>

FIG. 1 and FIG. 3 show a cell culturing device having one cell culturing vessel 1 in order to show it simply. As the cell culturing device of the present example as a whole, however, it is possible to carry out culturing of a large amount of cells by loading a plurality of cell culturing vessels and successively carrying out switching of electromagnetic valves and pumps to deliver a liquid.

Figure 7:
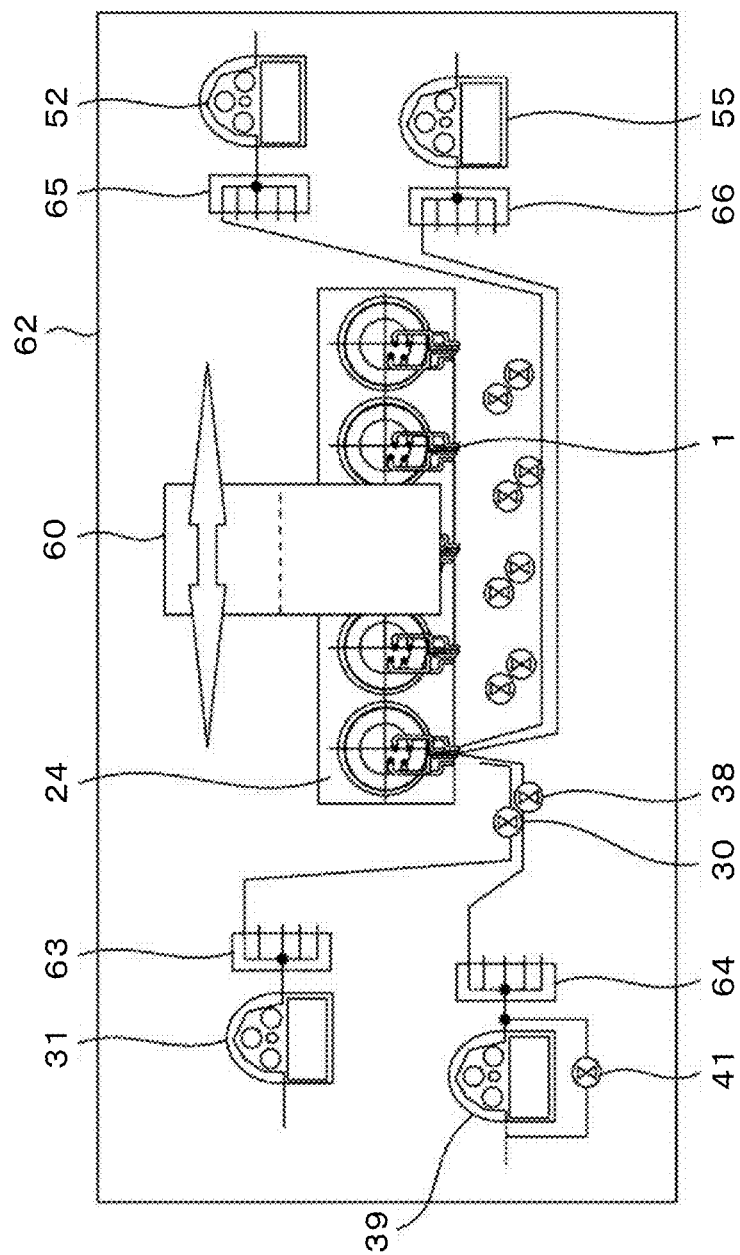
FIG. 7 shows the constitution of the cell culturing device that has a plurality of cell culturing vessels in First Example.

FIG. 7 is a top view of a cell culturing device 62 having a plurality of the cell culturing vessels 1 described in Example 1 on the upper surface of the stage 24. This drawing also shows the microscopic observation unit 60 and some of liquid delivery/discharge flow channels including rubber tubes, electromagnetic tubes, and roller pumps to be connected to the cell culturing vessels 1. Another constitution not shown here is similar to that of FIG. 3. When the number of the cell culturing vessels 1 is N, provided are a first pump branch 63 that can be branched into N pieces of flow channels between the first pump 31 and the first vessel open/close valve 30 of each of the cell culturing vessels; a second pump branch 64 that can be branched into N pieces of flow channels between the second pump 39 and the second vessel open/close valve 38 of each of the cell culturing vessels; a fourth pump branch 65 that can be branched into N pieces of flow channels between the second port 18 of each of the cell culturing vessels and the fourth pump 52; and a third pump branch 65 that can be branched into N pieces of flow channels between the fourth port 20 of each of the cell culturing vessels and the third pump 55.

Even when the cell culturing device has a plurality of the cell culturing vessels, liquid delivery/gas delivery necessary for cell culture can be achieved by operating the first vessel open/close valve 30 and the second vessel open/close valve 38 of each of the cell culturing vessels while referring to the flow chart in FIG. 4A and the liquid delivery/gas delivery time chart in FIG. 4B.

In the example of FIG. 7, five cell culturing vessels 1 are placed in series on the stage 24. The microscopic observation unit 60 moves in parallel to the linear stage 24 in an arrow direction and observes cells in each of the cell culturing vessels 1. At this time, the first to fourth ports are placed in an outward direction relative to the stage 24 (lower direction in FIG. 7). As a result, the first to fourth ports are placed only in a region on one side of the center 02 of the insert vessel 11 (in a lower-side region in FIG. 7) and at the same time, they are placed in an outer portion of the stage (lower side in FIG. 7) so that the liquid can be delivered without causing a difficulty in controlling the movement of the microscopic observation unit 60 along the linear stage 24. Further, since the ports are placed as described above, the insert vessel 11 eccentrically placed in the cell culturing vessel 1 is placed on the farther side (upper side in FIG. 7) of the stage 24, a cell observation range can be limited to a range closer to the microscopic observation unit 60. This enables a reduction in the size of the stage 24 and therefore, a reduction in the size of the automatic culturing device 62 itself.

<Taking-Out of Cultured Cells>

After completion of cell culture, the connection between the cell culturing device and the cell culturing vessel 1 should be released. In the present example, the first port 17, the second port 18, the third port 19, and the fourth port 20 of the cell culturing vessel 1 are each connected to a flow channel in the automatic device through a rubber tube. The cell culturing vessel 1 can be taken out from the cell culturing device by blocking the middle of the rubber tube with a rubber-tube closing member such as clamp and cutting a portion of the blocked tube on the farther side from the cell culture with sterilized scissors or the like. Alternatively, the connection between the cell culturing vessel and the cell culturing device may be released by making use of a member, so-called joint, provided in the middle of the rubber tube to enable a closed system.

The automatic culturing device is controlled, inside thereof, at a temperature of 37° C. If it takes long hours to release the connection, the temperature of the cell culturing vessel which has not yet been taken out may decrease due to long opening hours of a door or the like provided to keep the temperature of the vessel constant. In the present example, the first port 17, the second port 18, the third port 19, and the fourth port 20 of the cell culturing vessel 1 are placed in a region on one side of the center line of the insert vessel 11 and they are orderly placed in the outer portion of the stage 24, facilitating recognition of the rubber tube of the intended cell culturing vessel and release of the connection.

For cell culture, maintenance of a temperature environment is important. Culturing cells while retaining them in a vessel that covers the entirety of the culture dish 5 to keep air tightness is disadvantageous from the standpoint of heat transfer efficiency, because a material used for the formation of an airtight vessel should have an increased thickness. Using such a vessel has an influence on, for example, increase in heating time until cells reach a predetermined culturing temperature. In the cell culturing vessel 1 of Example 1, on the other hand, the culture dish 5 is exposed from the outer surface of the vessel in a region facing to the opening portion 3 of the bottom surface of the main vessel 2 and the heat transfer from the outside air is performed through the bottom surface of the culture dish 5. This means that in the cell culturing vessel 1 of Example 1, the culture dish having a minimum thickness necessary to actualize tissue culture and keep the air tightness of the culturing vessel is exposed from the outer surface of the air-tight vessel so that it is excellent in temperature management inside the vessel.

After the cell culturing vessel 1 is taken out from the cell culturing device, the cultured cells are taken out aseptically in a sterilized area and used for transplantation or the like. Cell culture is performed in an antiseptic area such as CPC and transplantation is also performed in an antiseptic operating room. CPC and the operating room are however not always adjacent to each other. The cultured cells are therefore often transported in an ordinary hospital corridor while being retained in a cell culturing vessel. When they pass through an area which is neither antiseptic nor clean, sterility of the outer surface of the cell culturing vessel is not ensured no matter how the vessel itself is airtight. It is therefore essential to prevent the culture medium from leaking from the vessel and touching the outer surface of the cell culturing vessel, when cells are taken out from the culturing vessel.

In the present example, the space in the cell culturing vessel 1 is kept airtight by providing the lid member 15 thereof with the first port 17, the second port 18, the third port 19, and the fourth port 20 and fixing the lid member 15 to the main vessel 2 from above through connection by a screw provided in the lid fixing ring 16. When the cultured cells are taken out, the cell culturing vessel is allowed to stand on an unillustrated hot plate to keep the temperature and connection with a screw is released by turning the lid fixing ring 16. The connection by a screw is released by the horizontal rotating operation while allowing the cell culturing vessel 1 to stand so that no external force is applied to the culture medium and the medium is prevented from spilling.

The lid member 15 of the cell culturing vessel 1 is, via the O ring 14, fixed to the main vessel 2 under pressure through connection by a screw provided in the lid fixing ring 16. The culture dish 5 is, via the rubber sheet 4, fixed to the main vessel 2 under pressure by connection between the pressing member 6 and the main vessel 2. Even when cultured cells are taken out as described above by releasing the connection by the screw of the lid fixing ring 16, fixing of the culture dish 5 under pressure is independent from the fixing of the lid member under pressure 15 by screwing so that fixing of the culture dish 5 under pressure is maintained. Such a structure is effective for taking out cultured cells antiseptically because it prevents leakage of the culture medium retrained in the culture dish 5 and limits a leakage range when the cultured cells are taken out.

The cell culturing vessel 1 described in First Example is made of a plastic such as polycarbonate, polystyrene or polypropylene so that it can withstand various sterilization techniques and effective for keeping it antiseptic prior to use for cell culture. Examples of the sterilizing method usable here include sterilization with a peracetic acid sterilizing agent, ethanol sterilization, aqueous hydrogen peroxide sterilization, and sterilization using an ethylene oxide gas sterilizer.

Further, the cell culturing vessel 1 can withstand various sterilizing techniques so that except components of a culture dish or insert vessel which cannot be repeatedly used, it can be used again, depending on use by repeating washing and sterilization after use. This leads to reduction in industrial waste.

A method of preparing a corneal epithelial tissue by using the cell culturing vessel of First Example for cell culture of a corneal epithelium and results of it will next be described.
<Method of Manufacturing Closed-System Cell Culturing Vessel>

Of the cell culturing vessel shown in FIG. 1, the main vessel 2, the pressing member 6, the lid member 15, and the lid fixing ring 16 were made by injection molding while using PC as a material. As the 0 ring 14, a JIS S-60 (width: 2 mm, inner diameter: 59.5 mm) was used and the rubber sheet 4 was obtained by punching a silicon rubber. As the culture dish 5, a 35-mm surface-treated cell culture dish, Catalog Number: 430165, product of Corning Incorporated was used. As the insert vessel 11, a cell culture insert (six-well type), Catalog Number: 353090, product of BD Corp. was used. A temperature responsive culture surface was made by electron beam polymerization of the substance permeable membrane 9 with N-isopropylacrylamide, a temperature responsive macromolecular monomer. It was con-firmed that adhesion and desorption of the corneal epithelial cells were performed normally on the present culture surface.

The above-mentioned components were assembled antiseptically in a safe cabinet to manufacture a cell culturing vessel. After the cell culturing vessel was put in a sterilization bag and sealed, it was placed in an ethylene oxide gas sterilizer, Catalog Number: EC-800, product of Sakura Seiki, followed by sterilization treatment based on the handling procedures of the sterilizer.
<Preparation of Corneal Epithelial Cell>

A method of culturing corneal epithelial cells will next be described. On a day before culturing corneal epithelial cells, as feeder cells, NIH-3T3 cells treated with mitomycin (10 µg/ml) at 37° C. for 2 hours were suspended, as feeder cells, in a culture medium to give a concentration of $2 \times 10^4/cm^2$ and the resulting suspension was retained in a cell bag of the second cell liquid 46. As corneal epithelial cells, corneal epithelial cells collected in a conventional manner from the corneal limbus of a rabbit eyeball purchased from Funakoshi Corporation were suspended in a culture medium to give a concentration of $4 \times 10^4/cm^2$ and retained in a cell bag of the first cell liquid 37. As media including the above-mentioned ones, a 5% FBS-containing KCM medium was used. It was retained in a culture medium bottle, that is, the culture medium 48, and was retained in a refrigerator 26 of the device.
<Start of Culture of Corneal Epithelial Cell>

Ten cell culturing vessels manufactured as described above were placed in an automatic culturing device, corresponding to the cell culturing device 62, placed in CPC. After the electromagnetic valves and the cell culturing vessels were connected to each other through a rubber tube, constant temperature maintenance of the automatic culturing device at 37° C. was started. After the device was allowed to stand for one hour, automatic culturing operation was started. The liquid delivery amount to the upper layer was 1.5 mL and the liquid delivery amount to the lower layer was 2.5 mL. Since a liquid delivery flow rate of a pump was 5 mL/min, the total operation time of the pump for the upper layer was set at 18 seconds and that for the lower layer was set at 30 seconds. At the time of discharging, the liquid delivery amount from the upper layer was set at 3 mL and that from the lower layer was set at 4 mL in order to discharge the liquid completely. The humidity of the $CO_2$ gas was adjusted to 95% H and the gas was delivered at a gas delivery flow rate of 1 L/min. The opening time of the electromagnetic valve was set at 5 seconds (50 mL) for injecting the gas in an amount exceeding the internal volume, that is, 37 $cm^3$, of the cell culturing device. The above-mentioned operation time chart was based on the outline of FIG. 4B.

Medium replacement was performed once a day on Day 5, Day 7, Day 9, Day 10, Day 11, Day 12, Day 13, Day 14, Day 15, and Day 16. The $CO_2$ gas delivery was performed four times a day, that is, every six hours. Microscopic observation was performed once every day from Day 5. Ten areas were obtained from each of the lower-layer cells and upper-layer cells of each of the cell culturing vessels and used as data for determining the cell growth state.
<Collection of Corneal Epithelial Tissue>

After medium replacement operation on Day 16, cell culture was finished and the cell culturing vessels were taken out as described above. The cell culturing vessels were placed in a safety cabinet and allowed to stand at room temperature (about 25° C.) for 30 minutes. The cell insert vessel was taken out as described above. Then, the sheet-like cells were separated and collected from the surface of the substance permeable membrane by using, as a support film, a hydrophilic PVDF membrane (product of Millipore) cut into doughnut shape.

<Control Test Method>

As the culture dish, a cell culture insert companion plate, Catalog Number: 353502, product of BD Biosciences having six wells (well inner diameter: 35 mm) in a 2-inch×3-inch plate was used. As the insert vessel 11, an insert vessel similar to that described above was used. As the temperature environment and $CO_2$ gas environment in cell culture, a $CO_2$ incubator, Catalog Number: MCO19-AIC, product of Sanyo Electric was used to set the temperature, humidity and $CO_2$ concentration at 37° C., 93% H, and 5%, respectively, and cell culture was performed. As control cells, cells similar to those used above were used.

Cell seeding and medium replacement were manually performed and the liquid amount added using a sterilized messpipette was equal to that described above. The frequency and interval of medium replacement were set equal to those in the above Example and control of the $CO_2$ gas was performed under equal conditions throughout culturing. The medium replacement was performed by placing the companion plate on a hot plate of 37° C. to maintain the temperature.

(Culture Test Results)

The ten sheet-like cells of the corneal epithelial tissue prepared using the cell culturing vessels of the present example were equal in size and thickness, showing that the vessels enable stable separation and collection. Also in comparison of microscopic images during growth, there was no significant difference in the growth of ten cells. On the other hand, cultured cells obtained by the control test and collected were equal in shape.

Cultured cells were observed by preparing sections of the corneal epithelial tissue and subjecting them to hematoxylin-eosin staining and immunohistostaining. As a result, it was found that a CK protein family known to be expressed in epithelial cells was expressed in all the cells in the present example group and the control test group. The CK3 known to be expressed in differentiated corneal epithelial cells were expressed in a portion of the cells other than the basal layer and Claudin 1, a closed binding protein necessary for the barrier function of the epithelial tissue, was expressed in the outermost layer. Also in this point, there was no difference between two groups.

With regard to the first problem in the constitution of a culture dish to be observed and a cell observation unit, the cell culturing vessel of the invention has no obstacle that disturbs an observation visual field of a microscope or the like because the culture dish having transparency is exposed and opposed to the outer surface of the closed culturing vessel. In addition, the first to fourth ports are collectively placed in one side of the center of the first vessel to maximize the observation visual field. This enables clear observation of the growth state of cultured cells.

With regard to the second problem, in medium replacement, an old medium is discharged, followed by addition of a new medium so that remaining of the old medium is prevented. In the culture medium discharge operation, the discharge port is placed at the lowest point of the culture dish and when the culturing vessel is retained at an arbitrary angle, the medium to be replaced gathers at the lowest point of each of the vessels, facilitating discharge by suction. In addition, since the center of the first vessel is eccentric to the center of the second vessel, the surface tension of the culture medium generated on the inside wall is small and the remaining amount of the culture medium decreases when the culture medium discharge operation is performed. When the culturing vessel is tilted, a collection amount of the old medium which has remained between the inside bottom portion of the first vessel and the outside bottom portion of the second vessel can be increased by providing the opening end for medium discharge in the vicinity of the outside bottom portion of second vessel.

With regard to the third problem, the surface condition can be kept stable because a surface-treated culture dish that is used manually as the first vessel for culturing cells can be used. This leads to stable cell culture. This culture dish is commercially available and a surface treatment cost can be reduced by using such a culture dish.

With regard to the fourth problem, that is, contamination from the outside, culturing vessels and channels use a completely closed system and do not have a structure exposed outside the culturing vessel so that invasion of microorganism-containing particles from the outside can be prevented. In addition, in the internal structure of the cell culturing vessel, the pressing member of it has a hollow node portion acting as a side wall of the first vessel so that splash generated during seeding of the feeder cell liquid in the first vessel can be prevented from reaching the inside of the second vessel with the node portion as a barrier.

Further, when cultured cells are taken out from the cell culturing vessel after completion of the cell culture, the cultured cells can be collected while minimizing the leakage of the culture medium. By using these means, cell culture can be performed stably. In addition, by providing a unit capable of easily observing the cultured condition and also providing a completely-closed-system automatic cell culturing unit, cells can be cultured antiseptically.

Example 2

The cell culturing vessel of Example 1 and the cell culturing device using it can also be applied to single-layer culture that uses only the culture dish 5 by partially changing the constitution.

Figure 8:
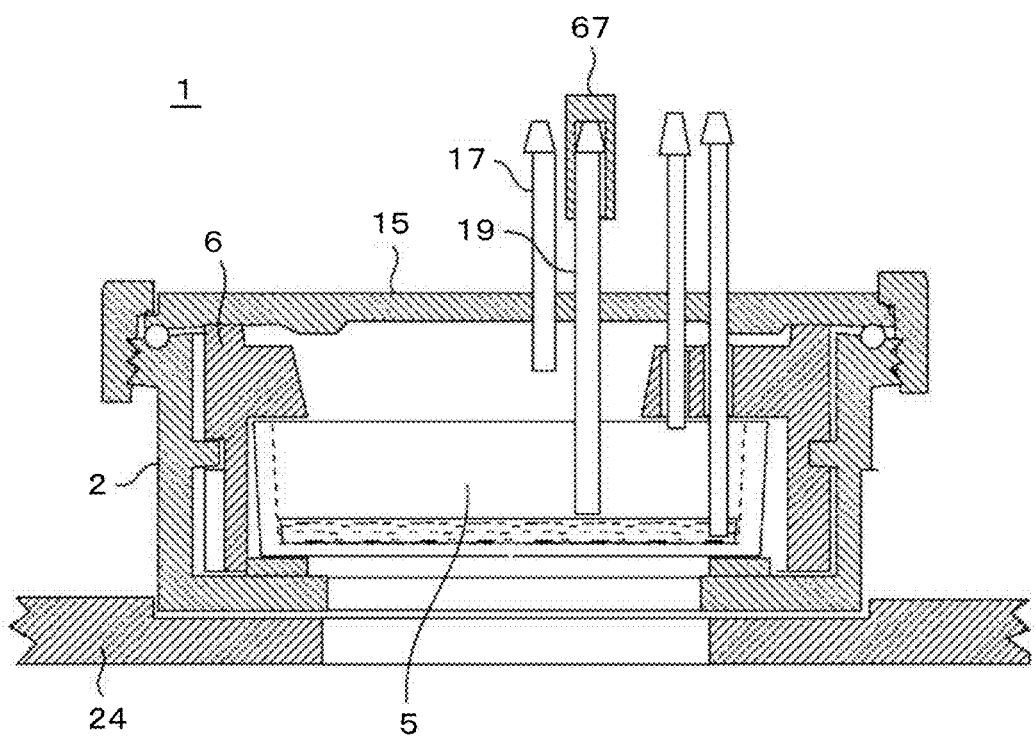
FIG. 8 shows the structure of a cell culturing vessel of Second Example of the invention.

FIG. 8 shows a culturing vessel similar to the cell vessel 1 described in Example 1 except that it does not have the insert vessel 11 but has only the culture dish 5. Also in single-layer culture, cell adhesion performance to the culture surface and the problem in cell observation during culturing are similar to those in double-layer culture. Necessity in automatic culture using single-layer culture is also similar.

As described in Example 1, fixing, under pressure, of the culture dish 5 to the main vessel 2 of the cell culturing vessel 1 is independent from the fixing of the lid member 15 with screw under pressure so that even when the insert vessel 11 is removed, the fixing, under pressure, of the culture dish 5 to the main vessel 2 is maintained and they have an airtight constitution. In this case, the first port 17 provided on the lid member 15 for injection into the insert vessel is necessary for regulating the atmospheric pressure in the cell vessel when cells are seeded in the culture dish 5. The second port 18 is, on the other hand, used only for discharging the culture medium from the insert vessel 11 so that this port is not necessary in single-layer culture for which the insert vessel 11 is not placed. The device is therefore constituted so as to enable selection, through a controller, from two operation modes, that is, a single-layer culture operation mode and a double-layer culture mode. In the double-layer culture mode, a constitution similar to that of Example 1 is employed, while in the single-layer culture operation mode, a cap 67 is attached to the second port 18 to release the connection with the fourth pump 52 and further, the first cell addition operation, the upper-layer medium addition operation, and the upper-layer medium discharge operation in the example of the liquid delivery/gas delivery method using the cell culturing vessel 1 described in FIG. 3 are omitted. For example, by changing an operation sequence so as not to operate a roller pump connected between the second port 18 and the fourth pump 52 involved in upper-layer medium discharge, automatic culture through single-layer culture using only the culture dish 5 can be performed without changing the constitution employed in the double-layer culture mode.

Even the single-layer culture of the present example has an advantage similar to that of the double-layer culture of Example 1.

Example 3

Since the insert vessel 11 is placed in the culture dish 5 in the cell culturing vessel of Example 1 and the cell culturing device using it, improvement is sometimes necessary for sufficiently collecting the remaining culture medium from the culture dish 5 by means of the fourth port 20.

In the present example, a fourth port having a constitution suited for sufficiently collecting a remaining culture medium is provided.

Figure 9A:
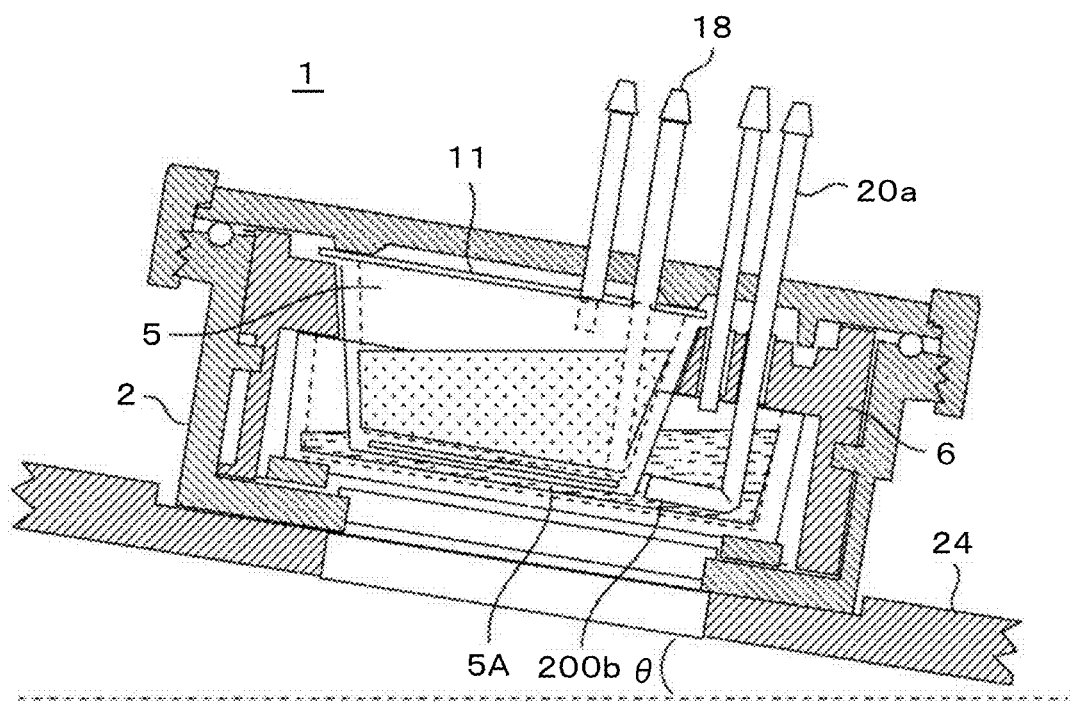
FIG. 9A shows the structure of a cell culturing vessel of Third Example of the invention.

With regard to a fourth port 20a shown FIG. 9A, the fourth port 20a is L-shaped so that the opening end 200a thereof is located at the lowest point of the outside bottom portion 5A of the insert vessel 11. During medium discharge, a culture medium sometimes remains due to surface tension between the outside bottom portion 5A of the insert vessel 11 and the inside bottom portion of the culture dish 5, depending on the culture medium to be used or the surface condition of the culture dish. In such a case, providing, as in the L-shaped fourth port 20a, the opening end 200a for medium discharge in the vicinity of the lowest point of the outside bottom portion of the insert vessel 11 when the cell culturing vessel 1 is tilted is effective for discharge of the culture medium between the outside bottom portion of the insert vessel 11 and the inside bottom portion of the culture dish 5.

Figure 9B:
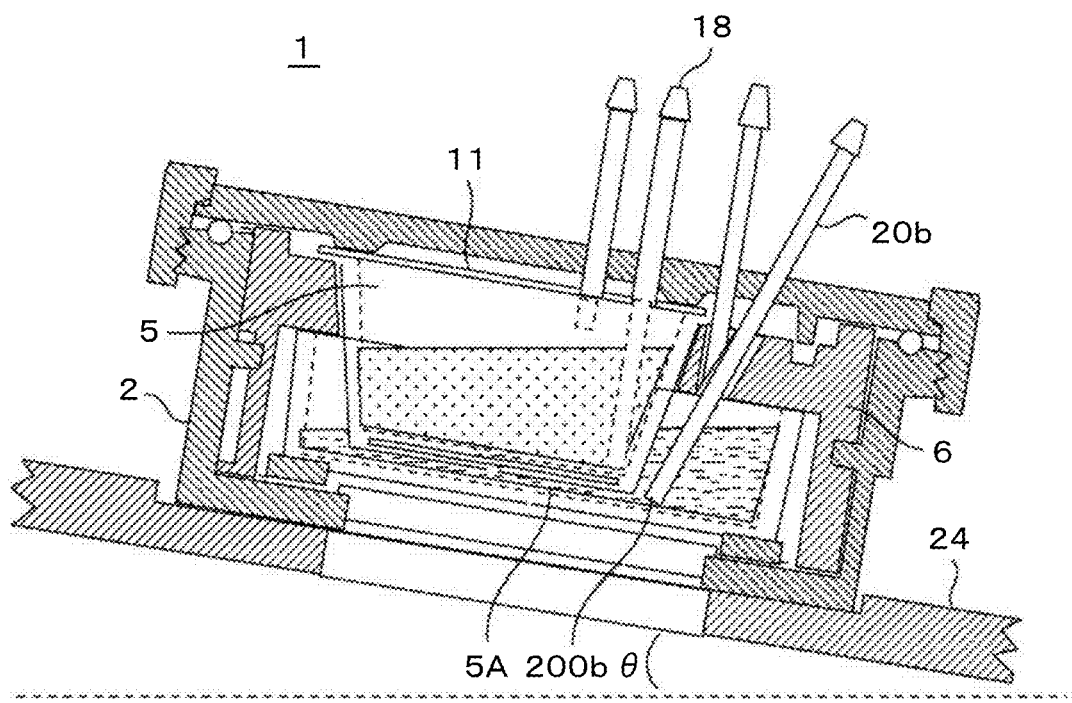
FIG. 9B shows another constitution example of the cell culturing vessel of Third Example.

In the structure shown in FIG. 9B, the fourth port 20b is placed in a through-hole tilted to the lid member 15 and the pressing member 6 so that the opening end 200b of it comes close to the bottom portion 5A of the insert vessel 11. The first to fourth ports 4 extend in an up-and-down direction relative to the lid member. The first to third ports extend in a direction agreeing with the central axis of the cell culturing vessel 1 and the fourth port extends in an up-and-down direction of the cell culturing vessel 1 at an angle tilted to the central axis.

In this tilted structure, when the cell culturing vessel 1 is tilted, the opening end 200b for medium discharge is located in the vicinity of the lowest point of the bottom portion 5A of the insert vessel 11. This example is also effective for medium discharge.

Example 4

In the cell culturing vessel of Example 1 and the cell culturing device using it, the through-hole 10 provided at the node portion 9 of the pressing member 6 and having the insert vessel 11 in the through-hole has an inverse truncated conical shape. The present invention is characterized by that a commercially available insert vessel can be used as the insert vessel 11 and the shape of the insert vessel 11 is not limited to an inverse truncated conical one. The shape of the through-hole 10 may be determined, depending on the outer shape of the insert vessel 11 to be used.

Figure 10:
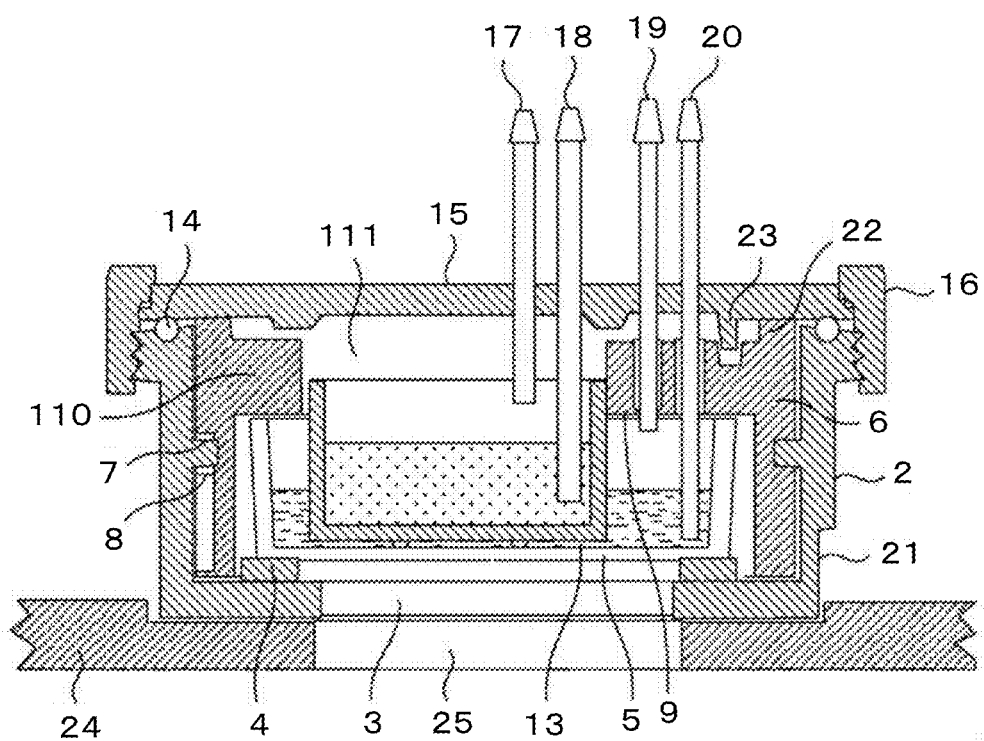
FIG. 10 shows the longitudinal plane of a cell culturing vessel of Fourth Example of the invention.

An insert vessel 111 of Example 4 shown in FIG. 10 has a cylindrical outer shape. In this case, a hole 110 provided at the node portion 9 is cylindrical corresponding to the outer shape of the insert vessel 11.

Assuming that the diameter of the culture dish 5 is represented by D10, the diameter of the through-hole of the node portion 9 of the pressing member 6 is represented by D20, and the diameter (outer diameter) of the insert vessel 11 is represented by D30, they satisfy the following relationship:

$$D10 > D20 > D30$$

This means that the diameter D20 of the through-hole provided in the pressing member is smaller than the inner diameter D10 of the culture dish (first vessel) 5 and greater than the outer diameter of the insert vessel (second vessel) 11.

The cell culturing vessel is similar to that of Example 1 in another constitution. For example, the center (O2) of the insert vessel 11 is made slightly eccentric to the center (O1) of another part (culture dish 5, pressing member 6).

The present example also has an advantage similar to that of Example 1.

1: CELL CULTURING VESSEL, 2: MAIN VESSEL, 3: OPENING PORTION, 4: RUBBER SHEET, 5: CULTURE DISH, 6: PRESSING MEMBER, 7: FITTING PROTRUSION, 8: FITTING GROOVE, 9: NODE PORTION, 11: INSERT VESSEL, 12: FLANGE PORTION, 13: SUBSTANCE PERMEABLE MEMBRANE, 14: O RING, 15: LID MEMBER, 16: LID FIXING RING, 17: FIRST PORT (INJECTION INTO INSERT VESSEL), 18: SECOND PORT (DISCHARGE FROM INSERT VESSEL), 19: THIRD PORT (INJECTION INTO CULCUTE DISH), 20,20A,20B: FOURTH PORT (DISCHARGE FROM CULTURE DISH), 21: POSITIONING GROOVE, 22: POSITIONING HOLE, 23: POSITIONING PIN, 24: STAGE, 25: OBSERVATION OPENING PORTION, 26: REFRIGERATOR, 30: FIRST VESSEL OPEN/CLOSE VALVE, 31: FIRST PUMP, 32: FIRST EXHAUST OPEN/CLOSE VALVE, 33: FILTER, 34: FIRST CELL OPEN/CLOSE VALVE, 35: FIRST MEDIUM SWITCHING VALVE, 36: FIRST CELL PRESSURE REDUCING VALVE, 37: FIRST CELL LIQUID, 38: SECOND VESSEL OPEN/CLOSE VALVE, 39: SECOND PUMP, 40: SECOND EXHAUST OPEN/CLOSE VALVE, 41: SECOND GAS OPEN/CLOSE VALVE, 42: SECOND CELL OPEN/CLOSE VALVE, 43: FIRST GAS OPEN/CLOSE VALVE, 44: SECOND MEDIUM SWITCHING VALVE, 45: SECOND CELL OPEN/CLOSE VALVE, 46: SECOND CELL LIQUID, 47: PREHEATING MECHANISM, 48: CULTURE MEDIUM, 49: LIQUID MEDIUM PRESSURE REDUCING VALVE, 50: HUMIDIFICATION BOTTLE, 51: DIOXIDE BOTTLE, 52: FOURTH PUMP, 53: FOURTH VESSEL OPEN/CLOSE VALVE, 54: UPPER-LAYER WASTE-LIQUID BOTTLE, 55: THIRD PUMP, 56: THIRD VESSEL OPEN/CLOSE VALVE, 57: LOWER-LAYER WASTE-LIQUID BOTTLE, 60: MICROSCOPIC OBSERVATION UNIT, 61: LIGHT IRRADIATION, 62: AUTOMATIC CULTURING DEVICE, 63: FIRST PUMP BRANCH, 64: SECOND PUMP BRANCH, 65: THIRD PUMP BRANCH, 66: FOURTH PUMP BRANCH, 67: CAP, 70: CONTROLLER

What is claimed is:

1. A cell culturing vessel for holding and culturing cells, comprising:
   a first vessel that stores therein a culture medium and cells or only a culture medium,
   a second vessel that is provided above the first vessel and stores a culture medium and cells or only a culture medium,
   a main vessel that holds the first vessel and houses the second vessel, and
   a lid member that engages with the main vessel,
   wherein the main vessel comprises a pressing member that fixes and holds the first vessel in the main vessel, and wherein the second vessel is eccentrically held in the first vessel by the pressing member.

2. The cell culturing vessel according to claim 1,
   wherein the lid member of the culturing vessel is equipped with a plurality of ducts that can be connected to an outside flow channel;
   wherein the ducts are placed in a region on one side of the center of the second vessel and opposite to the center of the first vessel.

3. The cell culturing vessel according to claim 2,
   wherein the ducts are first, second, third and fourth ducts extending in an up-and-down direction relative to the lid member,
   wherein the first duct is for injection to the second vessel,
   wherein the second duct is for discharge from the second vessel,
   wherein the third duct is for injection to the first vessel,
   wherein the fourth duct is for discharge from the first vessel, and
   wherein the second duct and the fourth duct are placed on the same straight line in a radius direction.

4. The cell culturing device according to claim 2,
   wherein the pressing member has therein a through-hole, and
   wherein the diameter of the through-hole is smaller than the inner diameter of the first vessel and greater than the outer diameter of the second vessel.

5. The cell culturing vessel according to claim 4,
   wherein the first vessel is fixed under pressure in the main vessel by using the pressing member to press the upper surface of the first vessel, and
   wherein the second vessel is fixed under pressure to the pressing member by using the lid member to press the second vessel inserted in the through-hole.

6. The cell culturing vessel according to claim 2,
   wherein the pressing member has a hollow node portion that acts as a side wall of the first vessel,
   wherein the second vessel has a flange to be retained on the upper surface of the side wall, and
   wherein assuming that a height of the first vessel from the inside bottom surface to the upper surface thereof is represented by H1, a perpendicular distance of the node portion between the lower surface and the upper surface thereof is represented by H2, a height of the second vessel from the bottom surface to the flange thereof is represented by H3, and a height from the bottom surface of the second vessel to the inside bottom of the first vessel is represented by H4, they satisfy the following relationship:

$H1+H2 \approx H3+H4$.

7. The cell culturing vessel according to claim 3,
   wherein the fourth duct that discharges a culture medium from the first vessel has an opening end thereof in the vicinity of the lowest point of the outer surface of the second vessel.

* * * * *